(12) United States Patent
Jones et al.

(10) Patent No.: US 9,552,457 B2
(45) Date of Patent: Jan. 24, 2017

(54) REPROGRAMMING EFFECTOR PROTEIN INTERACTIONS TO CORRECT EPIGENETIC DEFECTS IN CANCER

(71) Applicant: BRITISH COLUMBIA CANCER AGENCY BRANCH, Vancouver (CA)

(72) Inventors: Steven J. M. Jones, Vancouver (CA); Oleksandr Yakovenko, Vancouver (CA); Silvia Thoene, Vancouver (CA); Pierre Yulmin Cheung, Vancouver (CA); Jianghong An, Vancouver (CA)

(73) Assignee: BRITISH COLUMBIA CANCER AGENCY BRANCH, Vancouver (CA)

( * ) Notice: Subject to any disclaimer, the term of this patent is extended or adjusted under 35 U.S.C. 154(b) by 0 days.

(21) Appl. No.: 14/381,588

(22) PCT Filed: Feb. 27, 2013

(86) PCT No.: PCT/CA2013/050145
§ 371 (c)(1),
(2) Date: Aug. 27, 2014

(87) PCT Pub. No.: WO2013/127011
PCT Pub. Date: Sep. 6, 2013

(65) Prior Publication Data
US 2015/0154345 A1 Jun. 4, 2015

Related U.S. Application Data

(60) Provisional application No. 61/637,282, filed on Apr. 24, 2012, provisional application No. 61/603,650, filed on Feb. 27, 2012.

(51) Int. Cl.
| | | |
|---|---|---|
| G06F 19/16 | (2011.01) | |
| A61K 31/137 | (2006.01) | |
| A61K 31/47 | (2006.01) | |
| A61K 31/46 | (2006.01) | |
| A61K 31/10 | (2006.01) | |
| A61K 31/135 | (2006.01) | |
| A61K 31/167 | (2006.01) | |
| A61K 31/245 | (2006.01) | |
| A61K 31/36 | (2006.01) | |
| A61K 31/407 | (2006.01) | |
| A61K 31/5375 | (2006.01) | |
| C40B 30/02 | (2006.01) | |
| G06F 19/00 | (2011.01) | |
| A61K 31/343 | (2006.01) | |
| A61K 31/4709 | (2006.01) | |

(52) U.S. Cl.
CPC ............. *G06F 19/16* (2013.01); *A61K 31/10* (2013.01); *A61K 31/135* (2013.01); *A61K 31/137* (2013.01); *A61K 31/167* (2013.01); *A61K 31/245* (2013.01); *A61K 31/343* (2013.01); *A61K 31/36* (2013.01); *A61K 31/407* (2013.01); *A61K 31/47* (2013.01); *A61K 31/4709* (2013.01); *A61K 31/5375* (2013.01); *C40B 30/02* (2013.01); *G06F 19/706* (2013.01)

(58) Field of Classification Search
None
See application file for complete search history.

(56) References Cited

U.S. PATENT DOCUMENTS

| | | | |
|---|---|---|---|
| 3,257,274 A | 6/1966 | Loprieno et al. | |
| 3,466,274 A | 9/1969 | De Ridder | |
| 3,622,580 A | 11/1971 | Hromatka et al. | |
| 2009/0137508 A1 | 5/2009 | McSwiggen et al. | |
| 2011/0237606 A1 | 9/2011 | Chai et al. | |
| 2011/0251216 A1 | 10/2011 | Chinnaiyan et al. | |
| 2012/0071418 A1 | 3/2012 | Copeland et al. | |

FOREIGN PATENT DOCUMENTS

| | | |
|---|---|---|
| CA | WO 2013059944 | 5/2013 |
| EP | 0156785 A1 | 10/1985 |
| EP | WO20120123119 A1 | 9/2012 |
| GB | WO 2010064019 | 6/2010 |
| WO | 2007136790 A2 | 11/2007 |
| WO | WO2009015283 A2 | 1/2009 |
| WO | WO 2010045199 | 4/2010 |
| WO | WO 2010094009 | 8/2010 |
| WO | WO 2011014825 | 2/2011 |
| WO | WO20110143669 A2 | 11/2011 |
| WO | WO2012071469 A2 | 5/2012 |
| WO | WO20120116170 A1 | 8/2012 |

OTHER PUBLICATIONS

Mund et al. Bioassays, 32: 949-957, 2010.*
New Zealand Intellectual Property Office, Office Action issued in New Zealand Patent Application No. 700058, Aug. 17, 2015, 4 pages.
European Patent Office, Search Report issued in European Patent Application No. 13754077.9, Sep. 25, 2015, 6 pages.
Santiago, C., et al., "Druggability of Methyl-Lysine Binding Sites," Journal of Computer-Aided Molecular Design, vol. 25, No. 12, Dec. 7, 2011, pp. 1171-1178.

(Continued)

*Primary Examiner* — Michael Borin
(74) *Attorney, Agent, or Firm* — Laura M. Lloyd; Leech Tishman Fuscaldo & Lampl

(57) ABSTRACT

Methods of "reprogramming" epigenetic mark readers or erasers to recognize epigenetic marks other than their cognate (or natural) marks are provided. Reprogramming the reader or eraser can offset the effects of aberrant writer activity (for example, loss of function or overactivity) that can contribute to certain diseases states, such as cancer. The use of the reprogramming compounds identified by these methods in the treatment of such disease states is also provided. Exemplary mark readers that can be targeted by these methods include BPTF and CBX2.

13 Claims, 14 Drawing Sheets

(56) References Cited

OTHER PUBLICATIONS

Lutz, Robert E., et al., "Antimalarials α-Alkyl and Dialkylaminomethyl-2-phenyl-4-quinolinemethanols", Journal of the American Chemical Society, vol. 68, No. 9, Sep. 1, 1946, pp. 1813-1831.
Berendsen, H. et al., "Interaction Models for Water in Relation to Protein Hydration," B. Pullman (ed.), Intermolecular Forces, 1981 pp. 331-342, D. Reidel Publishing Company.
Berendsen, H. J. C. et al., "Molecular dynamics with coupling to an external bath," J. Chem. Phys. 181(8), Oct. 15, 1984, pp. 3684-3690, American Institute of Physics.
Campagna-Slater, V. et al., "Pharmacophore Screening of the Protein Data Bank for Specific Binding Aite Chemistry", J. Chem. Inf. Model., Mar. 2010, 50 (3), pp. 358-367, American Chemical Society.
Cerny, V., "Thermodynamic Approach to the Traveling Salesman Problem: An Efficient Simulation Algorithm," JOTA vol. 45, No. 1, Jan. 1985, pp. 41-51, Plenum Publishing Corporation.
Dimmock, J. R., et al., "Cytotoxic and anticancer activities of somel-aryl-2-dimethylaminomethyl-2-propen-I-one hydrochlorides", Pharmazie, 1998, 53(10), 702-706.
Essmann, U. et al., "A smooth particle mesh Ewald method," J. Chem. Phys. 1995, 103:8577-8593.
Grauffel, C. et al., "Force field parameters for the simulation of modified histone tails", J. Comput. Chem., Oct. 2010, 31 (13), pp. 2434-2451, Wiley Periodicals, Inc.
Gui, et al., "Frequent mutations of chromatin remodeling genes in transitional cell carcinoma of the bladder," 2011, Nat. Genet. 43:875-878.
Herold, J. M. et al., "Drug discovery toward antagonists of methyl-lysine binding proteins", Current Chem. Genomics, Aug. 2011, 5 (Suppl-M2), pp. 51-61, Bentham Open.
Hoover, W., "Canonical dynamics: Equilibrium phase-space distributions," Physical Review A 1985, 31:1695-1697, The American Physical Society.
Humphrey, W.; et al., "VMD: Visual Molecular Dynamics," J. Mol. Graph. 1996, 14:33-8, 27-8, Elsevier Science Inc.
Kaustov, L. et al., "Recognition and specificity determinants of the human Cbx chromodomains", Journal of Biological Chemistry, Jan. 7, 2011, 286 (1), 521-529.
Kirkpatrick, S. et al., "Optimization by Simulated Annealing," Science 1983, 220:671-680.
Kunkel, M.W. et al., "Cell line-directed screening assay for inhibitors of thioredoxin reductase signaling as potential anti-cancer drugs" Anti-Cancer Drug Design, 1997, 12(8), 659-670, Oxford University Press.
Lemkul, J. A. et al., "Practical Considerations for Building GROMOS-Compatible Small Molecule Topologies," J. Chem. Inf. Model. 2010, 50:2221-2235, American Chem. Society.
Li H., et al., "Structural Basis for Lower Lysine Methylation State-Specific Readout by MBT Repeats of L3MBTL1 and an Engineered PHD Finger," 2007, Mol. Cell., 28:677-691, Elsevier Inc.
Li, H., et al., "Molecular basis for site-specific read-out of histone H3K4me3 by the BPTF PHD Finger of NURF," 2006, Nature, 442:91-95, Nature Publishing Group.
Liu, D. C. et al., "On the Limited Memory BFGS Method for Large Scale Optimization," J. Math. Program. 1989, 45:503-528.
Mai, A. et al., "Epi-drugs to fight cancer: From chemistry to cancer treatment, the road ahead," Int. J. Biochem. Cell. Biol., 2009, 41:199-213, Elsevier Ltd.
Marx, K. A. et al., "Data mining the NCI cancer cell line compound GI50 values: identifying quinone subtypes effective against melanoma and leukemia cell classes", Journal of Chemical Information and Computer Sciences, 2003, 43(5), 1652-1667, Am. Chem. Soc.
Morin, et al., "Frequent mutation of histone-modifying genes innon-Hodgkin lymphoma," 2011, Nature 476: 298-303, Macmillan Publishers Limited.
Morin, et al., "Somatic mutation of EZH2 (Y641) in Follicular and Diffuse Large B-cell Lymphomas of Germinal Center Origin," 2010, Nat. Genet., 42(2):181-185, NIH.
Musselman, C. A. et al., "PHD fingers: epigenetic effectors and potential drug targets", Mol. Interv., Dec. 2009, 9 (6), 314-323.
Ng, S. S. et al., "Dynamic protein methylation in chromatin biology", Cell. Mol. Life Sci., Feb. 2009, 66 (3), 407-422.
Nose, S. et al., "Constant pressure molecular dynamics for molecular systems," Mol. Phys. 1983, 50:1055-1076.
Nose, S., "A molecular dynamics method for simulations in the canonical ensemble," Mol. Phys. 2002, 100:191-198, Taylor & Francis Ltd.
Parrinello, M. et al., "Polymorphic transitions in single crystals: A new molecular dynamics method," J. Appl. Phys. 1981, 52:7182-7190.
Pasqualucci, L. et al., "Analysis of the coding genome of diffuse large B-cell lymphoma," Nat. Genet. Jul. 31, 2011; 43(9):830-837, Nature America, Inc.
Pati, H. N. et al., "α-Substituted I-Aryl-3-dimethylaminopropanone Hydrochlorides: Potent Cytotoxins towards Human WiDr Colon Cancer Cells", Chemical & Pharmaceutical Bulletin, 2007, 55(4), 511-515, Pharmaceutical Society of Japan.
Quinn, A. M. et al., "Methods for Activity Analysis of the Proteins that Regulate Histone Methylation", Current Chemical Genomics., 2011, 5 (Suppl. I-M6), 95-105, Bentham Open.
Rotili, D. and Mai, A., "Targeting Histone Demthylases: A Newe Avenue for the Fight Against Cancer," 2011, Genes & Cancer, 2:663-679.
Ruthenburg et al., "Recognition of a mononucleosomal histone modification pattern by BPTF via multivalent interactions," 2011, Cell, 145(5):692-706, Elsevier, Inc.
Schuttelkopf, A. W. et al., "PRODRG: a tool for high-throughput crystallography of protein-ligand complexes," Acta Cryst. D Biol. Crystallography 2004, 60:1355-1363, International Union of Crystallography.
Scott, W. et al., "The GROMOS Biomolecular Simulation Program Package," J. Phys. Chem. A 1999, 103, 3596-3607, American Chemical Society.
Sneeringer, et al., "Coordinated activities of wild-type plus mutant EZH2 drive tumor-associated hypertrimethylation of lysine 27 on histone H3 (H3K27) in human B-cell lymphomas," 2010, Proc. Natl. Acad. Sci. U. S. A., 107:20980-20985, Epizyme, Inc.
Watanabe, et al., "Frequent Alteration of MLL3 Frameshift Mutations in Microsatellite Deficient Colorectal Cancer," PLoS One, Aug. 2011, vol. 6, Issue 8, e23320, pp. 1-8.
Yap, et al., "Somatic mutations at EZH2 Y641 act dominantly through a mechanism of selectively altered PRC2 catalytic activity, to increase H3K27 trimethylation," Blood, Feb. 24, 2011, vol. 117, No. 8, pp. 2451-2459, The American Society of Hematology.
Ziemin-Van Der Poel, et al., "Identification of a gene, MML, that spans the breakpoint in 11q23 translocations associated with human leukemias," Proc. Natl. Acad. Sci. USA vol. 88, pp. 10735-10739, Dec. 1991 Medical Sciences.
British Columbia Cancer Agency Branch, International Search Report and Written Opinion of the International Searching Authority, International Patent Application No. PCT/CA2013/050145, Canadian Intellectual Property Office, May 27, 2013.
Chemical Industry Press, "An Introduction to Computer-aided Drug Design", edited by Deyong Ye, pp. 34, 97-98 and 114-128, published on Jan. 31, 2004 (35 pages, including English Translation).
Chemical Industry Press, "New Methodology for Drug Synthesis", edited by Sanqi Zhang, pp. 16-19, published on May 31, 2009 (11 pages including English Translation).
Collier et al: "Synthesis, Molecular Modeling, DNA Binding, and Antitumor Properties of Some Substituted Amidoanthraquinones", Journal of Medicinal Chemistry, American Chemical Society, US, vol. 31, No. 4, Jan. 1, 1988 (Jan. 1, 1998), pp. 847-857, XP002063827, ISSN: 0022-2623,001: 10.1021/JM00399A028.
Dimmock et al: "Evaluation of acrylophenones and related bisMannich bases against murine P388 leukemia", European Journal of Medicinal Chemistry, Editions Scientifique Elsevier, Paris, FR, vol.

(56) References Cited

OTHER PUBLICATIONS

22, No. 6, Nov. 1, 1987 (Nov. 1, 1987), pp. 545-551, XP023871196, ISSN: 0223-5234, 001: 10.1016/0223-5234(87)90295-9 [retrieved on Nov. 1, 1987].
European Patent Office, European Search Report for European Patent Application No. 13754077.9, dated Feb. 19, 2016 (10 pages).
Fuchs et al: "Influence of Combinatorial Histone Modifications on Antibody and Effector Protein Recognition", Current Biology, Current Science, GB, vol. 21, No. 1,Nov. 23, 2010 (Nov. 23, 2010), pp. 53-58, XP028150458, ISSN: 0960-9822, 001: 10.1 016/J.CUB201 0.11.058 [retrieved on Nov. 25, 2010].
Medline Database [Online] US Nat. Library of Med. (NLM), Bethesda, MD, US; Feb. 1989 (Feb. 1989), Vigorita et al: "N-trifluoroacetyl derivatives as pharmacological agents. IV—Antiinflammatory and related properties; antimicrobial activity of some polyaromatic trifluoroacetamides," Database accession No. NLM2775414; Farmaco (Soc. Chimica Italiana: 1989) Feb. 1989, vol. 44, No. 2, Feb. 1989 (Feb. 1989), pp. 173-184, ISSN: 0014-827X (1 page).
Namkung: "Derivatives of fluorene. 34. N1-acetyl-N2-fluorenylasparagines", Journal of Medicinal Chemistry, Jan. 1, 1971 (Jan. 1, 1971), p. 467, XP55245358, Retrieved from the Internet: URL:http://pubs.acs.org/doi/pdf/1 0.1021 ljm00287a034 [retrieved on Jan. 27, 2016] (1 page).
New Zealand Intellectual Property Office, Office Action for New Zealand Patent Application No. 700058, dated May 3, 2016 (5 pages).
New Zealand Intellectual Property Office, Office Action for New Zealand Patent Application No. 700058, dated Aug. 31, 2016 (5 pages).
Pan et al., "Histone methylation and its relationship with cancer", Progress in Physiological Sciences, vol. 41, No. 1, pp. 22-26, published on Feb. 28, 2010 (11 pages incl. English Translation).
PubChem: "23654-93-5 I C12H1 002S—PubChem", Mar. 26, 2015 (Mar. 26, 2015), XP055245634, Retrieved from the Internet: URL:https://pubchem.ncbi.nlm.nih.gov/compound/305562#section=Chemical-Vendors [retrieved on Jan. 28, 2016] (13 pages).
PubChem: "2,3-dichloro-n-(9,1 0-dioxo-9, 1 0-dihydroanthracen-1-yl) propanamide I C17H11 CI2N03—PubChem", , Mar. 26, 2005 (Mar. 26, 2005), XP055245604, Retrieved from the Internet: URL:https://pubchem.ncbi.nlm.nih.gov/compound/73490#section=Biological-Test-Results [retrieved on Jan. 28, 2016] (12 pages).
State Intellectual Property Office of the People's Republic of China, Office Action dated Jun. 29, 2016 for Chinese Patent Application No. 201380011304.1 (50 pages).

\* cited by examiner

A.

B.
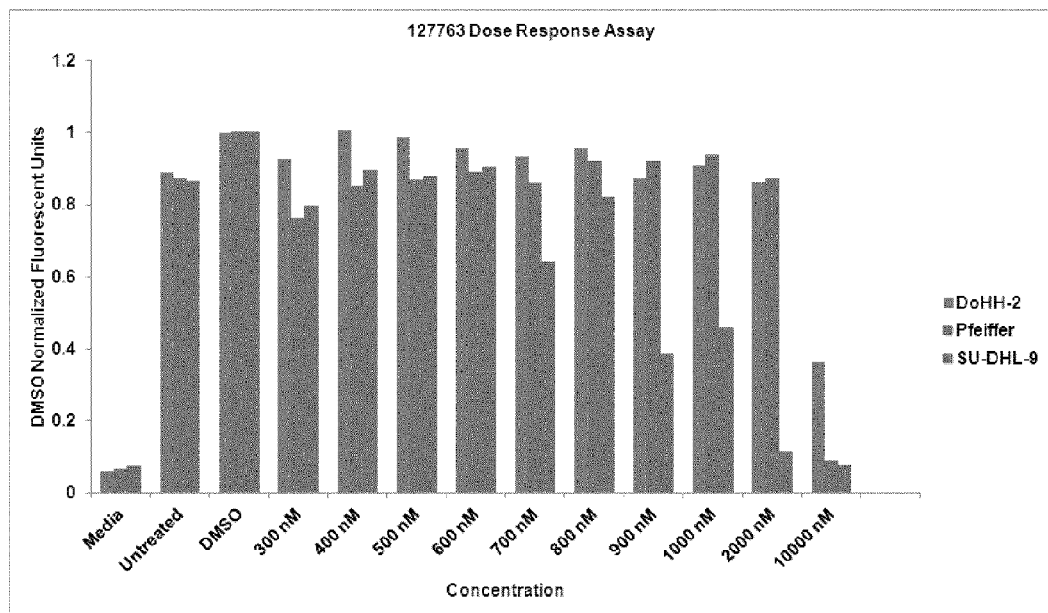
FIG. 2 (con.)

A.

B.

C.
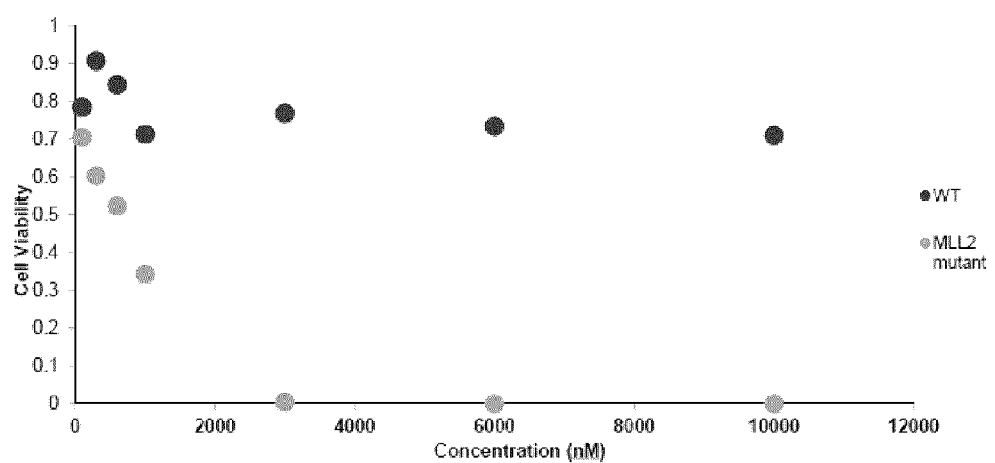
FIG. 3 (con.)

A.

B.

A.

B.

REPROGRAMMING EFFECTOR PROTEIN INTERACTIONS TO CORRECT EPIGENETIC DEFECTS IN CANCER

CROSS-REFERENCE TO RELATED APPLICATIONS

The present application is a national stage of International Patent Application No. PCT/CA2013/050145, titled "Reprogramming Effector Protein Interactions to Correct Epigenetic Defects in Cancer," filed Feb. 27, 2013, which claims the benefit of U.S. Provisional Patent Application No. 61/603,650 titled "Compositions and Methods of Treatment for Cancers Caused by Epigenetic Defects," filed Feb. 27, 2012; and U.S. Provisional Patent Application No. 61/637,282 titled "Reprogramming Effector Interactions to Correct Epigenetic Defects in Cancer," filed Apr. 24, 2012, the contents of which are incorporated in this disclosure by reference in their entirety.

FIELD OF THE INVENTION

The present invention relates to the field of therapeutics and, in particular, to methods, systems and assays involving small molecule compounds to indirectly correct oncogenic dysfunction and mutations in histone modifying genes for treatment of cancer or other disorders due to epigenetic de-regulation.

BACKGROUND OF THE INVENTION

Disruption of epigenetic mechanisms and pathways of gene regulation plays an important role in a spectrum of important disease states including cancer (Mai & Altucci, 2009, *Int. J. Biochem. Cell Biol.* 41:199-213).

Genome-wide screening for somatic mutations in non-Hodgkin's lymphoma (NHL) has shown a high prevalence of mutations in genes/proteins involved in epigenetic regulation of gene expression. Recurrent somatic mutations in the methyltransferase protein EZH2 were found to be likely to contribute to development of NHL through increased activity of the PRC2 of which it is a constituent protein. EZH2 is a histone mark "writer" that catalyzes the trimethylation of histone H3 lysine 27 (H3K27me3). NHL tumours with EZH2 mutations have been shown to have increased activity of the PRC2 in trimethylating histone H31(27 which leads to increased suppression of gene expression and tumourgenesis (Morin, et al., 2010, *Nat. Genet.*, 42(2): 181-185).

Overactivity and/or overexpression of EZH2 has been associated with a number of other cancers, including breast cancer, lung cancer, prostate cancer (in particular, late stage prostate cancer), multiple myeloma and cancers of the neurological system. In many cases, overactivity/overexpression of EZH2 has been associated with aggressive or drug resistant forms of these cancers. H3K27me3 marks are read by the protein CBX2.

The methyltransferase MLL2 writes activatory histone marks. This histone modification is interpreted by the reader protein BPTF. Mutations in MLL2 are also common in non-Hodgkin's lymphoma, with mutations being observed in 32% of DLBCL cases and 89% of follicular lymphomas (Morin, et al, 2011, *Nature* 476: 298-303). The mutational profile across MLL2 in these tumors was entirely consistent with a loss-of-function. MLL2 participates in laying down an activatory mark, H3K4me3 (Yap, et al, 2011, *Blood* 117:2451-2459; Sneeringer, et al, 2010, *Proc. Natl. Acad. Sci. U.S.A.* 107:20980-20985) and loss of this ability maintains the cells in a proliferative state, not by repression of a transcriptional program, but through the cells inability to activate a pro-differentiation transcriptional program. Mutations in MLL genes have also been found in gastric adenocarcinomas, leukemias, bladder and colorectal cancers (Gui, et al, 2011, *Nat. Genet.* 43:875-878; Watanabe, et al, 2011, *PLoS One* 6:e23320; Ziemin-van der Poel, et al, 1991, *Proc. Natl. Acad. Sci. U.S.A.* 88:10735-10739).

The ability of BPTF to read trimethylated H3K4 has been modulated by engineering a single tyrosine to glutamic acid substitution within the PHD finger domain of the protein, resulting in a reversal of the binding preference from trimethyl- to dimethyl-lysine in an H3K4 context (Li, et al., 2007, *Molecular Cell*, 28:677-691).

Inhibition or disruption of binding of histone mark readers has been reported as an approach for treating disease, including cancer. In particular, histone demethylases have been targeted for inhibition (see Rotili & Mai, 2011, *Genes & Cancer*, 2:663-679; International Patent Application Publication No. WO2012/071469).

International Patent Application Publication No. WO2011/143669 describes compounds and methods for disrupting the interaction of a bromodomain and extra-terminal (BET)-family protein with an acetyl-lysine modification on a histone N-terminal tail. Specifically, the compounds inhibit binding of the BET family protein to the acetyl-lysine. Uses of the compounds to treat cancer and inflammatory diseases are also described.

International Patent Application Publication No. WO2012/123119 describes in vitro methods employing biotin and strepavidin that allow for the identification of proteins interacting with histone tails and compounds that interact with such proteins.

International Patent Application Publication No. WO2012/116170 describes compounds that inhibit acetyl-lysine binding activity of the bromodomain of the CREB-binding protein (CBP).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates broadly to methods of reprogramming effector protein interactions to correct epigenetic defects in cancer.

In one aspect, the invention relates to a method for identifying candidate compounds that modulate binding of a histone mark reader protein to a histone tail, the method comprising: (a) computationally generating a structural model of the active site of the reader protein in complex with a target histone tail mark, the structural model based on a computational model of the active site of the reader protein complexed with its cognate histone tail mark; (b) identifying one or more functional features required for binding of the target histone tail mark in the active site of the reader protein; and (c) screening candidate compounds to identify those that together with the residues in the active site and the target histone tail mark, substantially reproduce the functional features identified in step (b).

In another aspect, the invention relates to a method for identifying candidate compounds that modulate binding of a histone methylation mark reader protein to a methylated histone tail, the method comprising: (a) computationally generating a structural model of the active site of the reader protein in complex with a target methylated histone tail mark, the structural model based on a computational model of the active site of the reader protein complexed with its cognate methylated histone tail mark; (b) identifying one or more functional features required for binding of the target methylated histone tail mark in the active site of the reader protein; and (c) screening candidate compounds to identify those that together with the residues in the active site and the target methylated histone tail mark, substantially reproduce the functional features identified in step (b).

In another aspect, the invention relates to a use of a compound of general Formula I to increase binding of BPTF to mono- or di-methylated lysine 4 of histone 3:

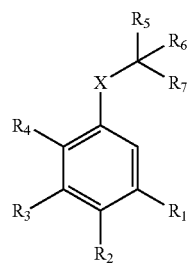

I wherein:

X is C=O or S(O)$_2$,

R$_1$ is H, C$_1$-C$_4$ alkyl or C$_1$-C$_4$ alkoxy,

R$_2$ is H, C$_1$-C$_4$ alkyl, C$_1$-C$_4$ alkoxy or halo, and R$_3$ is H, or R$_2$ and R$_3$ taken together with the C atoms they are attached to form:

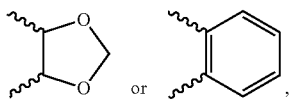

R$_4$ is H, C$_1$-C$_4$ alkyl, C$_1$-C$_4$ alkoxy, or halo,

R$_5$ is H, CH$_2$NMe$_2$ or

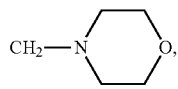

and

R$_6$ is H, and R$_7$ is H, or R$_6$ and R$_7$ taken together form =CH$_2$, wherein when R$_5$ is H and R$_6$ and R$_7$ taken together form =CH$_2$, X is S(O)$_2$, and wherein when R$_4$ is C$_1$ alkyl, R$_5$ is CH$_2$NMe$_2$, and R$_6$ and R$_7$ taken together form =CH$_2$, then at least one of R$_1$, R$_2$ and R$_3$ is other than H;

or (b) X is NH,

R$_1$ and R$_2$ are H,

R$_3$ and R$_4$ taken together with the C atoms they are attached to form:

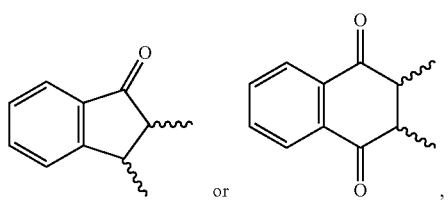

R$_5$ is substituted C$_1$-C$_4$ alkyl or unsubstituted C$_2$-C$_4$ alkyl, wherein each substituent is a halogen, and R$_6$ and R$_7$ taken together form =O.

In another aspect, the invention relates to a use of a compound of general Formula I as defined above in the manufacture of a medicament to increase binding of BPTF to mono- or di-methylated lysine 4 of histone 3.

In another aspect, the invention relates to a compound of general Formula I as defined above for use to increase binding of BPTF to mono- or di-methylated lysine 4 of histone 3.

In another aspect, the invention relates to a method of increasing binding of BPTF to mono- or di-methylated lysine 4 of histone 3 comprising contacting BPTF with a compound of general Formula I as defined above.

In another aspect, the invention relates to a use of a compound of general Formula I as defined above for the treatment of cancer.

In another aspect, the invention relates to a use of a compound of general Formula I as defined above in the manufacture of a medicament for the treatment of cancer.

In another aspect, the invention relates to a compound of general Formula I as defined above for use to treat cancer.

In another aspect, the invention relates to a method of treating cancer in a subject comprising administering to the subject a compound of general Formula I as defined above.

In another aspect, the invention relates to a use of a compound selected from the group consisting of:

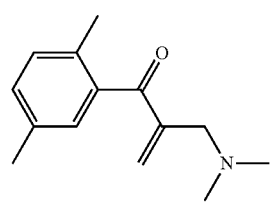

1

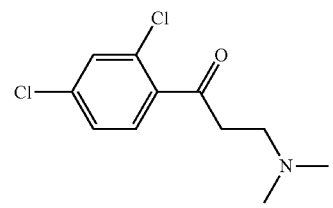

2

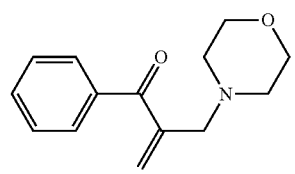

11

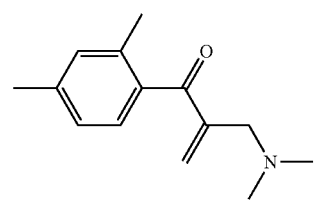

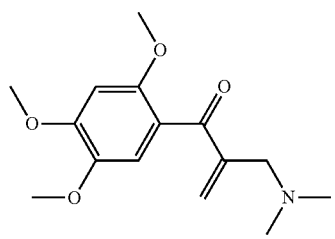

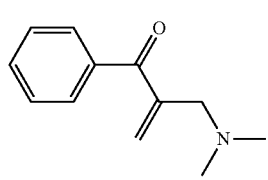

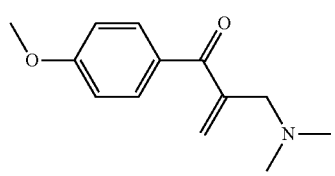

18

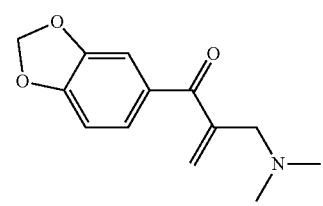

19

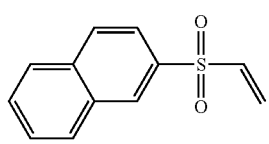

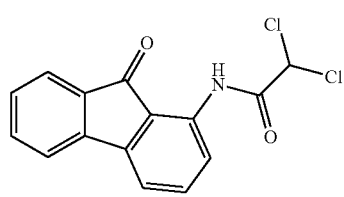

22

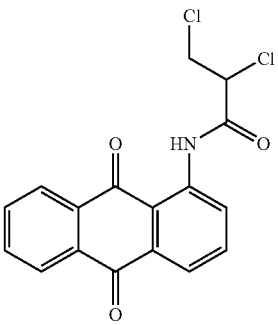

3

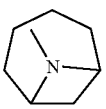

4

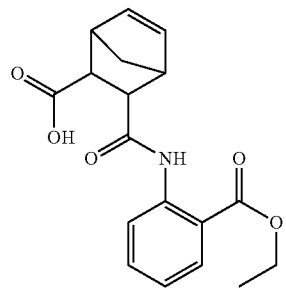

and

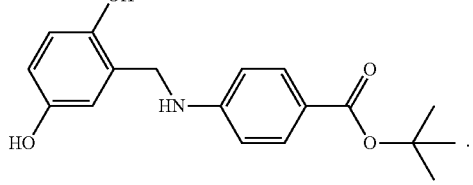

5

In another aspect, the invention relates to a use of a compound selected from the group defined above in the manufacture of a medicament to increase binding of BPTF to mono- or di-methylated lysine 4 of histone 3.

In another aspect, the invention relates to a compound selected from the group defined above for use to increase binding of BPTF to mono- or di-methylated lysine 4 of histone 3.

In another aspect, the invention relates to a method of increasing binding of BPTF to mono- or di-methylated lysine 4 of histone 3 comprising contacting BPTF with a compound selected from the group defined above.

In another aspect, the invention relates to a use of a compound selected from the group defined above for the treatment of cancer.

In another aspect, the invention relates to a use of a compound selected from the group defined above in the manufacture of a medicament for the treatment of cancer.

In another aspect, the invention relates to a compound selected from the group defined above for use to treat cancer.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
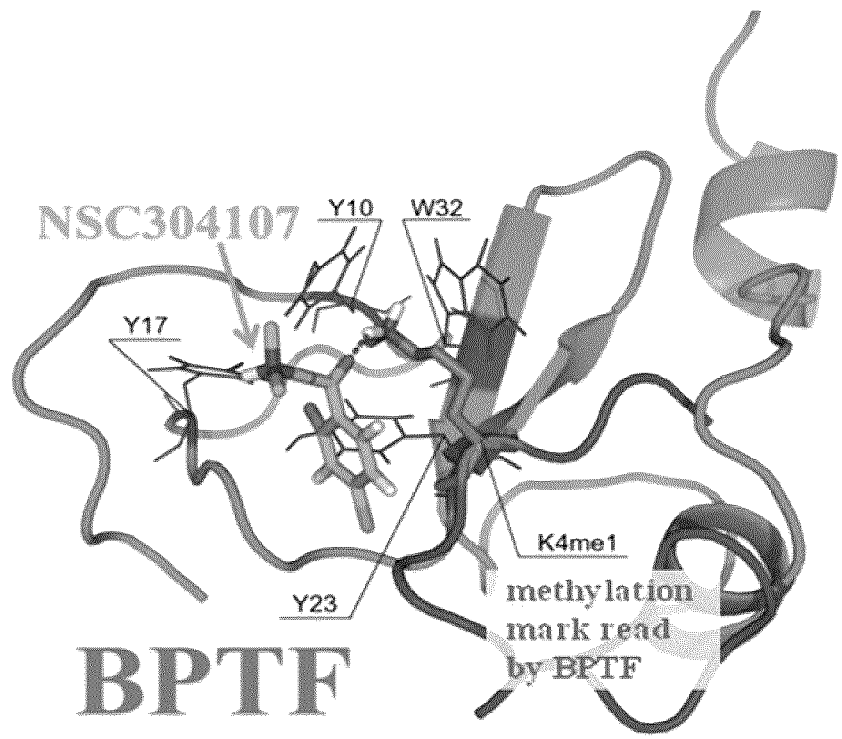
FIG. 1 presents a model of a "triple reprogramming complex" of BPTF, Compound 2 and the H3K4me1 peptide.

The present invention relates broadly to methods of "reprogramming" epigenetic mark readers or erasers to recognize epigenetic marks other than their cognate (or natural) marks. Reprogramming the reader or eraser in this way can offset the effects of aberrant writer activity (for example, loss of function or overactivity) that can contribute to certain diseases states. The reprogramming compounds identified by these methods thus have potential therapeutic applications in the treatment of such disease states.

In a broad aspect, therefore, the invention relates to a method to identify small molecule compounds that modify the affinity and/or selectivity of histone mark "readers" for their corresponding histone marks which are laid down by corresponding "writers." By altering the interaction between the reader protein and modified lysine residues on histones, through, for example, formation of a 'triple re-programming complex' between the histone lysine tail, the intervening small molecule compound and the lysine tail binding pocket on the mark reader, the histone mark signal transduced by the mark reader downstream (to effect gene expression, for example) can be advantageously changed/altered. Thus the small molecule compounds identified in this manner modulate the binding interaction between the modified lysine residues on histones (marks) laid down by mark writers and the mark signal effector proteins (readers) by introducing new binding interactions between the reader and the modified lysine residues. This method of using small molecule compounds to introduce new binding interactions (re-program) between histone epigenetic marks and the corresponding mark readers in order to modify the downstream signals transduced by certain histone marks may be applied to various writer/reader pairs of epigenetic signalling proteins. By altering the way histone mark readers transduce signals for various modified states of their substrate lysine residues on histones, the deleterious effects of pathogenic or aberrant epigenetic marks may be corrected or reversed in order to advantageously treat a disease state, such as cancer, wherein it has been shown the certain writers are mutated (causing changes in the level or type of mark) and these mutated writers are cancer drivers (i.e. contribute to or cause cancer).

The small-molecule histone mark reader 're-programming' compounds in accordance with the invention form a triple 're-programming complex' involving the histone/lysine tail, the intervening compound and the lysine tail binding pocket of the mark reader and may be identified by computational screening of small molecule 'virtual' compound libraries against docking structures comprising key binding residues in the modified lysine tail binding pocket of the reader and the lysine tail from the histone mark. Small molecule 're-programming' compounds may, for example, introduce new interactions between the reader protein and the histone/lysine tail comprising the epigenetic 'mark' and enable binding of the reader protein to the lysine tail despite the modification state of the lysine tail (mark). Small molecule 're-programming' compounds may either increase or decrease the affinity/binding of the reader protein for a particular lysine tail depending on the modification (for example, methylation) state of the lysine tail/mark. By virtue of new interactions established in this manner, small molecule 're-programming' compounds may change the substrate specificity of the mark reader for the particular mark (for example, a methylated histone lysine residue).

In one aspect of the invention, the histone mark reader is CBX2, which reads marks laid down by the histone mark writer EZH2 methyltransferase (a component of the PRC2 protein complex). EZH2 adds methyl groups to lysine residue 27 of histone H3 (H3K27). In general, EZH2 writes suppressive marks with the end result being suppression of gene activity. Increases in expression (and therefore mark writer activity) of wild-type EZH2 as well as certain somatic missense mutations (including, but not limited to, tyrosine residue 641) in EZH2 are known to alter the amount or valency (i.e. mono, di-, or tri-methylation) of methyl marks at H3K27. These changes in EZH2 lead to increased gene suppression relative to normal state and have been shown to be pathogenic and related to disease. In particular, they are likely oncogenic or driver changes/mutations for several types of cancer. CBX2 (a component of the PRC1 protein complex) acts as an effector for EZH2 methyl marks and is essential for transducing the repressive (or gene silencing) signal for EZH2 in normal function as well as in disease states where EZH2 expression or activity is altered. Using the methods described herein, small molecule compounds (reprogramming compounds) that will bind to the methylated-lysine binding pocket of CBX2 and change the substrate specificity of CBX2 for the methylated lysine 27 (H3K27) through formation of a triple reprogramming complex involving CBX2, the small-molecule compound and the methylated lysine tail have now been identified. These small molecule CBX2 re-programming compounds are shown to have anti-cancer activity against lymphoma (with Tyr-641 mutation) cells and tumours in vitro and in vivo. An advantage of these small molecule compounds that re-program the reader (CBX2) for EZH2 is that in principle they should be effective drugs able to correct disease causing (oncogenic in the case of cancer) changes in EZH2 marks independent of the perturbation in the writer (EZH2). These compounds therefore should have advantages over other compounds that directly target the EZH2 protein or EZH2 gene expression.

In another aspect of the invention, the histone mark reader is BPTF, which reads marks laid down by the histone mark writer MLL2 methyltransferase. MLL2 adds methyl groups to lysine residue 4 of histone H3 (H3K4). In general, MLL2 activity and resultant methyl histone marks are activating and result in increases in gene activity. Reductions in MLL2 gene expression or certain mutations of MLL2 are known to be related to disease states. In particular, loss-of-function (LoF) mutations in MLL2 are very frequent and likely to be oncogenic 'driver' mutations in non-Hodgkin lymphoma or other cancers. BPTF is an essential effector protein for transducing signals pertaining to the MLL2 writer protein in a downstream signalling pathway both in normal and disease states where MLL2 activity is perturbed. Using the methods described herein, small molecule reprogramming compounds that are able to change the substrate specificity of BPTF for the H3K4 methyl marks corresponding to the MLL2 writer have now been identified. Compounds have been identified that form a 'triple re-programming complex' between the compound, H3K4 marks and the methyl H3K4 binding pocket in BPTF with the result being to change the substrate specificity of the BPTF protein for the H3K4 mark. BPTF re-programming compounds identified by these methods are able to overcome and correct the oncogenic effects of perturbations in the MLL2 protein including reduced expression or loss-of-function mutations in the latter. These compounds should be effective drugs for treatment of lymphomas or other cancers caused by mutant MLL2 or reduced expression of MLL2. A particular advantage of the BPTF re-programming approach and compounds discovered by this means is that these are useful drugs for correcting defective epigenetic regulation and for treatment of diseases such as lymphoma involving loss of function mutations in MLL2 which are not directly targetable by small molecules.

In certain aspects of the invention, the small molecule re-programming of epigenetic mark readers as disclosed herein is useful for diseases or disorders involving perturbation or mutation of the HMTs EZH2 and MLL2, including but not limited to cancers such as lymphoma, lung cancer, breast cancer and neurological cancers.

In another embodiment of the invention, small molecules useful for the treatment of cancer or other disorders of epigenetic regulation (particularly histone modification) may be identified through the formation of triple reprogramming complexes to change the substrate specificity or binding affinity of methylated mark readers for methylated amino acid residues in histones.

Certain aspects of the invention relate to the application of the methods of the invention to other types/classes of epigenetic marks and their corresponding writers and readers, including but not limited to acetylation.

Another aspect of the invention relates to a biochemical binding assay to verify and confirm properties of re-programming compounds identified by methods of the invention disclosed herein to modify the substrate specificity or binding affinity of readers to various histone marks. This assay is based on the triple re-programming complex formed between the methylated histone lysine residue (mark), the mark reader methylated lysine binding pocket and the intervening small molecule re-programming compound. The binding assay measures the methylation state of a particular histone lysine residue "pulled down" with the corresponding reader protein in the presence or absence of a particular re-programming candidate compound.

Certain aspects of the invention relate to the application of the methods of the invention to other types/classes of epigenetic marks and their corresponding writers and histone mark 'erasers' (i.e. demethylases or deacetylases), whose biochemical function is to remove histone marks (methyl or acetyl groups). Small molecule compounds that bind to and/or interact with erasers to inhibit eraser activity are candidate drugs for treatment of cancer since it is known that many histone eraser proteins are over expressed in several different types of cancers. Examples of candidate histone mark eraser target proteins include LSD1 whose biochemical function is to remove methyl residues from the H3K4 (me2/1) methyl mark, PLU1 whose biochemical function is to remove methyl residues from the H3K4 (me3/2) methyl mark, GASC1 whose biochemical function is to remove methyl residues from the H3K9 (me3/2) methyl mark, and other H3K4 mark erasers the inhibition of which may correct or counteract the oncogenic effect of loss-of-function mutations in MLL2.

Another aspect of the invention relates to combinations of inhibitors of H3K4 erasers (including but not limited to LSD1 and PLU1) with small molecule BPTF re-programming compounds (as described herein) for treatment of cancers or other disorders due to loss of function mutations in the MLL2 histone methyltransferase.

Another broad aspect of the invention relates to the artificial simulation of MLL2 protein functions as an approach for the development of therapies for treatment of Non-Hodgkin's lymphomas (NHL) and other cancers.

Certain aspects of the invention relate to the transcription factor BPTF as a target for the development of therapies for treatment of Non-Hodgkin's lymphomas (NHL), the germinal centre B (GCB) subtype of diffuse large B-cell lymphoma (DLBCL) in which the histone methyltransferase protein MLL2 has LoF mutations, the activated B-cell-like (ABC) subtype of diffuse large B-cell lymphoma (DLBCL) in which the histone methyltransferase protein MLL2 has LoF mutations, and/or cancers with inactivated MLL2 protein, which include but are not limited to, lung cancer, breast cancer and cancers of the neurological system.

Certain aspects of the invention relate to the compounds NSC382001 (Compound 1), NSC304107 (Compound 2), NSC127763 (Compound 3), and others including but not limited to those listed in Tables 2, 3 and 4 herein, as compounds predicted to interact with or bind to the BPTF protein and thereby change the specificity of BPTF for methylated forms of lysine 4 of the Histone H3 protein.

Certain aspects of the invention relate to the compounds NSC382001 (Compound 1), NSC304107 (Compound 2), NSC127763 (Compound 3), and others including but not limited to those listed in Tables 2, 3 and 4 herein, as potential agents for treatment of NHL, ABC-DLBCL, GCB-DLBCL, and/or cancers with low active protein expression, including but not limiting to lung cancer, breast cancer and cancers of the neurological system.

Another aspect of the invention relates to the compounds NSC382001 (Compound 1), NSC304107 (Compound 2), NSC127763 (Compound 3), and others including but not limited to those listed in Tables 2, 3 and 4 herein, as potential new agents for treatment of NHL, ABC-DLBCL or GCB-DLBCL in which a) the histone methyltransferase MLL2 is mutated, b) the histone methyltransferase protein MLL2 has LoF mutations resulting in decreased trimethylation of lysine 4 residues in histone H3 or c) the MLL2 protein is of lower activity relative to normal state or wild-type.

A further aspect of the invention relates to BPTF interacting/binding compounds (including but not limited to NSC382001 (Compound 1), NSC304107 (Compound 2), NSC127763 (Compound 3), and others including but not limited to those listed in Tables 2, 3 and 4 herein) in combination with compounds that interact with/bind to the protein CBX2 (for example, those shown in Table 5 herein) for treatment of cancers in which both MLL2 has LoF mutations and EZH2 activity is increased (either through mutation or increased EZH2 protein expression). Examples include, but are not limited to, NHL, ABC-DLBCL, GCB-DLBCL, follicular lymphoma, lung cancer, breast cancer, prostate cancer and cancers of the neurological system.

Another aspect of the invention relates to compounds NSC382001 (Compound 1), NSC304107 (Compound 2), NSC127763 (Compound 3), and others including but not limited to those listed in Tables 2, 3 and 4 herein, in combination with standard of care therapy (targeted or non-targeted) or emerging therapies for treatment of cancers with reduced MLL2 protein activity (caused by LoF mutations for example), including but not limited to NHL, ABC-DLBCL, GCB-DLBCL, follicular lymphoma, lung cancer, breast cancer, prostate cancer and cancers of the neurological system. In certain embodiments, such combinations may further include compounds that interact with/bind to the protein CBX2 (for example, those shown in Table 5 herein).

DEFINITIONS

Unless defined otherwise, all technical and scientific terms used herein have the same meaning as commonly understood by one of ordinary skill in the art to which this invention belongs.

As used herein, the term "about" refers to an approximately +/−10% variation from a given value. It is to be understood that such a variation is always included in any given value provided herein, whether or not it is specifically referred to.

The term "plurality" as used herein means more than one, for example, two or more, three or more, four or more, and the like.

The use of the word "a" or "an" when used herein in conjunction with the term "comprising" may mean "one," but it is also consistent with the meaning of "one or more," "at least one" and "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

The terms "therapy" and "treatment," as used interchangeably herein, refer to an intervention performed with the intention of alleviating the symptoms associated with, preventing the development of, or altering the pathology of a disease. Thus, in certain embodiments, the terms therapy and treatment are used in the broadest sense, and in various embodiments may include one or more of the prevention (prophylaxis), moderation, reduction, and/or curing of a disease at various stages. Those in need of therapy/treatment thus may include those already having the disease as well as those prone to, or at risk of developing, the disease, disorder or condition and those in whom the disease is to be prevented.

The terms "subject" and "patient" as used herein refer to an animal in need of treatment.

The term "animal," as used herein, refers to both human and non-human animals.

Administration of the compounds of the invention "in combination with" one or more further therapeutic agents is intended to include simultaneous (concurrent) administration and consecutive administration. Consecutive administration is intended to encompass various orders of administration of the therapeutic agent(s) and the compound(s) of the invention to the subject with administration of the therapeutic agent(s) and the compound(s) being separated by a defined time period that may be short (for example in the order of minutes) or extended (for example in the order of days or weeks).

The term "$C_1$-$C_4$ alkyl" refers to a straight chain or branched alkyl group of one to four carbon atoms. Examples include methyl, ethyl, propyl, isopropyl, butyl, isobutyl, secbutyl and tert-butyl (t-butyl).

The terms "halogen" and "halo" refer to fluorine, bromine, chlorine, and iodine atoms.

The term "$C_1$-$C_4$ alkoxy" refers to the group —OR, where R is $C_1$-$C_4$ alkyl.

Target Proteins

Suitable target proteins for the methods of the invention include histone mark readers and erasers. Examples include, but are not limited to, the reader proteins CBX2, BPTF, HP1, 53BP1 and L3MBTL1 and histone Lys demethylase (KDM) eraser proteins belonging to the amino oxidase or the JmjC domain containing protein families, such as LSD1, PLU1, and GASC1.

In certain embodiments, the target protein is a histone mark reader, such as CBX2, BPTF, HP1, 53BP1 or L3MBTL1. In some embodiments, the target protein is a histone methylation mark reader.

In certain embodiments, the target protein is a histone methylation mark reader that preferentially recognizes a trimethylated lysine residue in the histone tail. Examples of such reader proteins include, but are not limited to BPTF, CBX2 and HP1.

In certain embodiments, the target protein is CBX2. CBX2 is also known as chromobox homolog 2, MGC10561, cell division cycle associated 6, M33, chromobox homolog 2 (*Drosophila* Pc class), CDCA6, chromobox homolog 2 (Pc class homolog, *Drosophila*), chromobox protein homolog 2, modifier 3 and Pc class homolog. Database identifiers for CBX2 include: UniProtKB/Swiss-Prot: CBX2_HUMAN, Q14781; HGNC: 15521 and Entrez Gene: 847332.

In certain embodiments, the target protein is BPTF. BPTF is also known as bromodomain PHD finger transcription factor, FAC1, Fetal Alzheimer antigen, FALZ, NURF301, Bromodomain and PHD finger-containing transcription factor, Fetal Alz-50 clone 1 protein and OTTHUMP00000163084. Database identifiers for BPTF include HGNC: 3581; Entrez Gene: 2186; Ensembl: ENSG00000171634; OMIM: 601819 and UniProtKB: Q12830.

Reprogramming Methods

In certain aspects, the present invention relates to computational methods for identifying candidate compounds that are able to modify the selectivity of the target protein for its cognate histone mark ("reprogramming compounds"). The compounds are identified on the basis that they are able to compensate for certain binding interactions that are present when the target protein binds the modified amino acid residue that constitutes its cognate histone tail mark, but are absent when the modification state of the residue is different. In general, the methods include generating a 'triple re-programming complex' between a modified histone lysine tail, the candidate compound and key residues in the active site of the target protein that binds the lysine tail.

While the reprogramming methods are described herein as embodiments relating to reader proteins, one skilled in the art will appreciate that the reprogramming may also be applied to eraser proteins and certain embodiments of the invention thus relate to methods of reprogramming eraser proteins.

In certain embodiments, the methods involve computationally generating a structural model of the active site of the reader protein in complex with the non-cognate histone tail mark that the reader is to be reprogrammed to bind (the "target histone tail mark"). This structural model is typically based on a known computational model of the active site of the reader protein complexed with its cognate histone tail mark in which one or more functional features that characterize binding of the cognate histone tail mark in the active site have been identified. By "functional features" it is meant features that contribute to the binding or stabilization of the cognate histone mark in the active site. Such features may include, for example, the presence or absence of certain non-covalent interactions, such as hydrogen bonds, van der Waals interactions, electrostatic interactions and/or hydrophobic interactions; the presence or absence of certain groups or residues, such as hydrogen bond donors, hydrogen bond acceptors, hydrophobic residues or groups, aromatic residues or groups; conformational features, such as the spacing between functional groups in the active site and/or the cognate histone mark, the length of aliphatic chains, and the like. Computational models of various reader protein active sites can be obtained from publicly accessible databases, such as the Protein DataBank maintained by Rutgers, The State University of New Jersey and the University of California, San Diego.

The structural model of the active site of the reader protein in complex with the target histone tail mark can then be used to identify one or more additional functional features required for binding of the target histone tail mark in the active site of the reader protein. For example, inspection r computational analysis of the model may indicate that additional functional features, such as hydrogen bonds or hydrophobic interactions, need to be added or removed in order to stabilize the target histone mark in the active site of the reader protein. Provision of such additional functional features by the candidate reprogramming compound should allow for binding of the target histone mark in the active site of the reader.

As trimolecular complexes are inherently entropically unfavourable when compared to bimolecular complexes, the final triple reprogramming complex containing the modified histone lysine tail, the candidate compound and key residues in the active site must account for the entropy loss associated with the trimolecular complex and the resulting free energy. This can be achieved, for example, through the use of a series of template ("probe") structures that are selected to bind non-competitively with the target histone mark and which can be iteratively refined while monitoring the behaviour of the system as a whole in order to identify the probe structure that provides the most energetically stable triple reprogramming complex.

Accordingly, in certain embodiments, to identify appropriate candidate compounds, a probe structure may be generated that provides the requisite functional features for a stable triple reprogramming complex. The probe structure may be generated, for example, by iteratively refining a series of probe structures using, for example, molecular dynamics simulations and/or visual inspection to identify a suitably stable structure. The structure of the final probe complexed in the active site can subsequently be used as a basis for identifying candidate compounds.

Candidate compounds may be identified, for example, by screening virtual libraries of compounds, such as those provided by the Zinc Database, the National Cancer Institute's Diversity Set, the National Cancer Institute's Open Chemical Repository, the Chembridge Library DIVERSet, the Maybridge Library, the Platinum Collection from Asinex and Natural Product Libraries.

Various methods are available to one skilled in the art for screening chemical compounds for their ability to provide the identified functional features. The overall process may begin, for example, with visual inspection of the active site and probe structure on the computer screen. Selected chemical compounds can then be positioned in a variety of orientations, or docked, within the active site to determine whether they adequately reproduce the functional features of the probe structure. Docking may be accomplished using various commercially available software, such as Quanta (Accelrys, Inc., Madison, Wis.), FlexX (TRIPOS, St. Louis, Minn.) and DOCK. Docking can be followed by energy minimization and molecular dynamics with standard molecular mechanics force fields, such as CHARMM and AMBER (Accelrys, Inc., Madison, Wis.). Other specialized computer programs known in the art and/or commercially available may also assist in the process of selecting candidate compounds.

Alternatively, candidate compounds that provide the appropriate functional features may be generated de novo using standard computational methods. Various de novo design methods are known in the art.

Once a compound has been designed or selected, the efficiency with which that compound may interact with the target histone mark and the reader's active site may be tested and optimized by computational evaluation if necessary. Specific computer software is available in the art to evaluate compound deformation energy and electrostatic interactions. Examples of programs designed for such uses include: AMBER, QUANTA/CHARMM (Accelrys, Inc., Madison, Wis.) and the like.

In Vitro Evaluation

Candidate compounds identified using the reprogramming methods described herein can be subsequently evaluated in vitro, for example, for their ability to modulate binding of the reader protein to the target histone mark and/or for activity in disease states (such as cancer) associated with aberrant activity of their cognate writer protein.

The ability of candidate compounds to modulate binding of the reader protein to the target histone mark can be assessed by various standard in vitro techniques such as surface plasmon resonance or fluorescence polarization.

Figure 4:
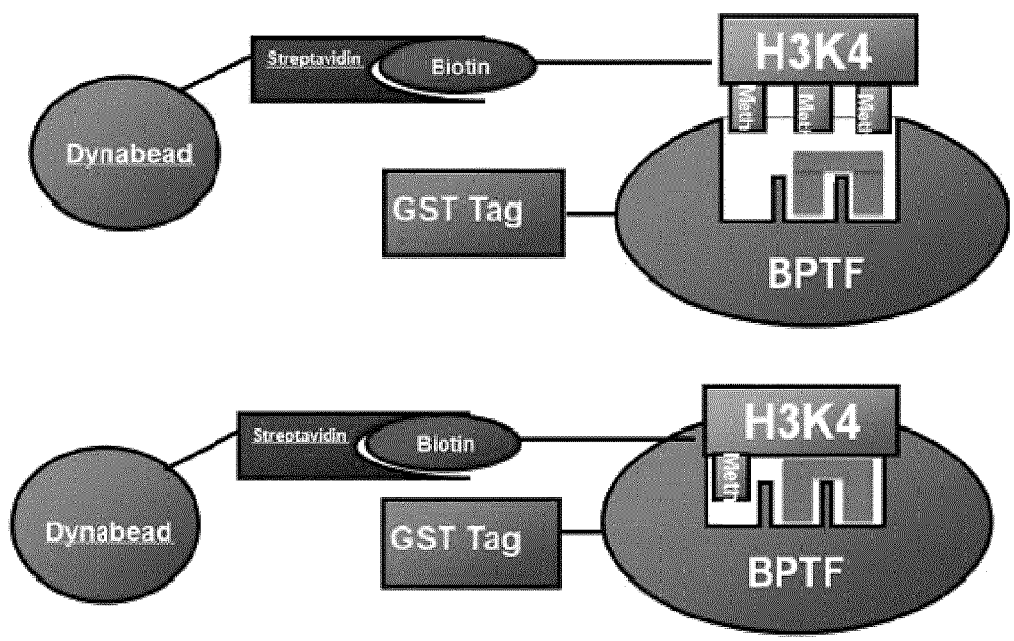
FIG. 4 presents a general schema of the BPTF pull down assay for assessing interaction with H3K4 methylated tails employed in Example 5. This schema depicts a compound that will stabilize binding of H3K4me1 and sterically hinder H3K4me3 binding.

Certain embodiments of the invention relate to the use of a "pull down" assay to characterize the binding of candidate compounds to the target mark. A general schema for such an assay as it applies to BPTF is shown in FIG. 4 and described in Example 5. Briefly, the GST-labeled PHD finger-bromodomain of BPTF was incubated with the candidate compound and H3K4me0, me1, me2 or me3 peptides that were coupled to streptavidin-labeled dynabeads through a biotin molecule on the peptide. After washing with an appropriate buffer, bound protein was eluted from the beads and assessed by SDS-PAGE and optionally Western blot. One skilled in the art will appreciate that this assay can be readily adapted to other readers/erasers and histone marks.

Alternatively, technologies such as the Alpha Technology developed by PerkinElmer may be employed to assess the ability of the candidate compounds to modulate the binding of the reader to the target histone mark. Such technologies can provide for such assessments to be conducted on a high-throughput basis. The Alpha Technology assay, for example, requires the use of Alpha donor beads conjugated with streptavidin and Alpha acceptor beads conjugated with glutathione. The interacting domain of the reader can be cloned into a construct that introduces a glutathione 5-transferase tag allowing for coupling with the Alpha acceptor bead via glutathione. Biotinylated histone peptides bearing specific epigenetic modifications can be purchased commercially and coupled with the Alpha donor beads via streptavidin. If the interacting domain binds to the histone peptide, the Alpha donor and acceptor beads will be brought into close proximity of one another so that when the donor bead is excited with light of a certain wavelength, it will emit oxygen molecules that then react with the acceptor bead causing it to generate chemiluminescence as an output signal for a binding interaction.

Various in vitro assays relating to the disease state (such as cancer) associated with aberrant activity of a writer protein may be used for evaluating the activity of the candidate compounds. For example, the cytotoxicity of the compounds can be assayed in vitro using a suitable cell line, typically a cancer cell line. In general, cells of the selected test cell line are grown to an appropriate density and the candidate compound is added. After an appropriate incubation time (for example, about 48 to 72 hours), cell survival is assessed. Methods of determining cell survival are well known in the art and include, but are not limited to, the resazurin reduction test (see Fields & Lancaster (1993) *Am. Biotechnol. Lab.* 11:48-50; O'Brien et al., (2000) *Eur. J. Biochem.* 267:5421-5426 and U.S. Pat. No. 5,501,959), the sulforhodamine assay (Rubinstein et al., (1990) *J. Natl. Cancer Inst.* 82:113-118) or the neutral red dye test (Kitano et al., (1991) *Euro. J. Clin. Investg.* 21:53-58; West et al., (1992) *J. Investigative Derm.* 99:95-100). Cytotoxicity is determined by comparison of cell survival in the treated culture with cell survival in one or more control cultures, for example, untreated cultures and/or cultures pre-treated with a control compound (typically a known therapeutic).

The ability of the compounds to inhibit proliferation of cancer cells in vitro can be assessed, for example, by culturing cells of a cancer cell line of interest in a suitable medium. After an appropriate incubation time, the cells can be treated with the candidate compound and incubated for a further period of time. Cells are then counted and compared to an appropriate control. Suitable controls include, for example, cells treated with a standard chemotherapeutic and/or untreated cells.

Alternatively, the compounds can be tested in vitro by determining their ability to inhibit anchorage-independent growth of tumour cells. Anchorage-independent growth is known in the art to be a good indicator of tumourigenicity. In general, anchorage-independent growth is assessed by plating cells from a selected cancer cell-line onto soft agar and determining the number of colonies formed after an appropriate incubation period. Growth of cells treated with the candidate compound can then be compared with that of control cells (as described above).

Various other assays known in the art may also be employed.

A variety of cancer cell-lines suitable for testing the candidate compounds are known in the art and many are commercially available (for example, from the American Type Culture Collection, Manassas, Va.).

If necessary, the toxicity of the compounds can also be initially assessed in vitro using standard techniques. For example, human primary fibroblasts can be treated in vitro with the candidate compound and then tested at different time points following treatment for their viability using a standard viability assay, such as the assays described above, or the trypan-blue exclusion assay. Cells can also be assayed for their ability to synthesize DNA, for example, using a thymidine incorporation assay, and for changes in cell cycle dynamics, for example, using a standard cell sorting assay in conjunction with a fluorocytometer cell sorter (FACS).

Pharmaceutical Compositions

Certain embodiments of the invention relate to pharmaceutical compositions comprising a reprogramming compound identified by the methods described herein and a pharmaceutically acceptable carrier, diluent, or excipient. The pharmaceutical compositions are prepared by known procedures using well-known and readily available ingredients.

The reprogramming compound or pharmaceutical compositions comprising the compound may be formulated for administration orally (including, for example, buccally or sublingually), topically, parenterally, by inhalation or spray, or rectally in dosage unit formulations containing conventional non-toxic pharmaceutically acceptable carriers, adjuvants and vehicles. Typically, the compound is incorporated into an acceptable vehicle and formulated into a form suitable for administration, such as syrups, elixirs, tablets, troches, lozenges, hard or soft capsules, pills, suppositiories, oily or aqueous suspensions, dispersible powders or granules, emulsions, injectables, or solutions. The term parenteral as used herein includes subcutaneous injections, intradermal, intra-articular, intravenous, intramuscular, intravascular, intrasternal, intrathecal injection or infusion techniques.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (for example, ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

For rectal administration, compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Other pharmaceutical compositions and methods of preparing pharmaceutical compositions are known in the art and are described, for example, in *"Remington: The Science and Practice of Pharmacy"* (formerly *"Remingtons Pharmaceutical Sciences"*); Gennaro, A., Lippincott, Williams & Wilkins, Philidelphia, Pa. (2000).

Uses

Certain embodiments of the invention relate to the use of the reprogramming compounds identified by the methods disclosed herein to indirectly correct dysfunction and mutations in histone modifying proteins for treatment of cancer or other disorders due to epigenetic de-regulation. In some embodiments the compounds modulate the binding activity of a histone mark reader or eraser protein such that the protein is able to bind to a mark other than its cognate mark. In this way, use of the compounds can offset or reverse the deleterious effects of aberrant writer activity that characterizes certain disease states such as cancer.

In certain embodiments, the reprogramming compound modulates the binding activity of a histone methylation reader and may, therefore, find utility in the treatment of diseases characterized by aberrant activity of a histone methyltransferase (writer), for example, EZH2 or MLL2.

Certain embodiments of the invention provide for the use of reprogramming compounds that modulate the binding activity of BPTF, for example, by increasing the ability of BPTF to bind to mono- or di-methylated H3K4, in the treatment of diseases characterized by decreased methylation activity of MLL2. For example, BPTF reprogramming compounds may be used in the treatment of cancer and, in particular in the treatment of cancers characterized by decreased methylation activity of MLL2. Cancers associated with loss of function mutations in MLL2 include, but are not limited to, Non-Hodgkin's lymphomas (NHL), the germinal centre B (GCB) subtype of diffuse large B-cell lymphoma (DLBCL), the activated B-cell-like (ABC) subtype of diffuse large B-cell lymphoma (DLBCL), and cancers with inactivated MLL2 protein include, but are not limited to, lung cancer, breast cancer and cancers of the neurological system.

Certain embodiments of the invention therefore relate to the use of BPTF reprogramming compounds to increase the ability of BPTF to bind to mono- or di-methylated H3K4 in a patient having NHL, GCB-DLBCL, ABC-DLBCL, lung cancer, breast cancer or a cancer of the neurological system.

Certain embodiments of the invention provide for the use of reprogramming compounds that modulate the binding activity of CBX2, for example by increasing the ability of CBX2 to bind to mono- or di-methylated H3K27, for the treatment of diseases characterized by increased methylation activity of EZH2. For example, CBX2 reprogramming compounds may be used in the treatment of cancer and, in particular in the treatment of cancers characterized by increased methylation activity of EZH2. Overexpression of EZH2 has been associated with a number of cancers, including breast cancer, prostate cancer, ovarian cancer, endometrial cancer, lung cancer, multiple myeloma, cancers of the neurological system and lymphomas. Some embodiments provide for the use of CBX2 reprogramming compounds in the treatment of aggressive, drug-resistant or refractory cancers which have been shown to be associated with overexpression of EZH2.

Certain embodiments of the invention relate to the use of CBX2 reprogramming compounds in the treatment of a cancer having a mutant form of EZH2, for example, a mutant form of EZH2 in which the tyrosine at position 641 is replaced with an alternate amino acid (a Y641 mutant). Examples of such cancers, include, but are not limited to, lymphomas (such as non-Hodgkin's lymphoma (NHL), follicular lymphoma (FL) and germinal centre B subtype of diffuse large cell lymphoma (GCB-DLBCL)), prostate cancer, breast cancer, lung cancer and cancers of the neurological system.

Combination Therapy

In certain embodiments of the invention relating to the use of a reprogramming compound for the treatment of cancer, the compound may be used in combination with one or more chemotherapeutic agents.

Various chemotherapeutic agents are known in the art and include those that are specific for the treatment of a particular type of cancer as well as those that are applicable to a range of cancers, such as doxorubicin, capecitabine, mitoxantrone, irinotecan (CPT-11), cisplatin and gemcitabine.

Chemotherapeutics typically used in the treatment of solid tumours include, for example, Gemicitabine (e.g. Gemzar®), Cyclophosphamide, Capecitabine (e.g. Xeloda®), Ifosfamide, Paclitaxel (e.g. Taxol®), Cisplatin, Docetaxel (e.g. Taxotere®), Carboplatin, Epi-doxorubicin (epirubicin), Doxorubicin (e.g. Adriamycin®) and 5-fluorouracil (5-FU).

Chemotherapeutics typically used in the treatment of breast cancer include, for example, Capecitabine (e.g. Xeloda®), Cyclophosphamide, 5-fluorouracil (5-FU), Carboplatin, Paclitaxel (e.g. Taxol®), Cisplatin, Docetaxel (e.g. Taxotere®), Ifosfamide, Epi-doxorubicin (epirubicin), Doxorubicin (e.g. Adriamycin®), Trastuzumab (Herceptin®) and Tamoxifen.

Chemotherapeutics typically used in the treatment of non-Hodgkin's lymphoma include, for example, Procarbazine (e.g. Matulan® CD), Cytarabine, Rituximab (e.g. Rituxan®) and Etoposide.

Chemotherapeutics typically used in the treatment of prostate cancer include, for example, Goserelin Acetate (e.g. Zoladex®), Mitoxantrone (e.g. Novantrone®), Prednisone (e.g. Deltasone®), Liarozole, Nilutamide (e.g. Nilandron®), Flutamide (e.g. Eulexin®), Finasteride (e.g. Proscar®), Terazosin (e.g. Hytrin®), Doxazosin (e.g. Cardura®), Cyclophosphamide, Docetaxel (e.g. Taxoter® CD), Estramustine and Luteinizing hormone releasing hormone agonist.

Some embodiments of the invention relate to the use of a reprogramming compound, such as a CBX2 or BPTF reprogramming compound, in combination with a therapeutic that targets EZH2 for the treatment of cancer. Examples of such compounds include, for example, those described in U.S. Patent Application Publication Nos. 2009/0137508, 2011/0251216, 2012/0071418 and 2011/0237606.

Certain embodiments of the invention relate to the use of a reprogramming compound, such as a CBX2 or BPTF reprogramming compound, in combination with a chemotherapeutic for the treatment of a drug resistant tumours where drug resistance is the result of upregulation/overactivity of EZH2.

Certain embodiments of the invention relate to the use of a BPTF re-programming compound in combination with an inhibitor of H3K4 erasers, such as LSD1 or PLU1, for treatment of cancers or other disorders due to loss of function mutations in MLL2.

Certain embodiments of the invention relate to the use of a BPTF re-programming compound in combination with a CBX2 reprogramming compound in the treatment of cancers with reduced MLL2 protein activity (caused by LoF mutations for example) and/or increased EZH2 activity, including but not limited to NHL, ABC-DLBCL, GCB-DLBCL, follicular lymphoma, lung cancer, breast cancer, prostate cancer and cancers of the neurological system.

Kits

Certain embodiments of the invention provide for kits containing one or more reprogramming compounds, for example, therapeutic packs or kits. In those embodiments in which the reprogramming compounds are intended for use as part of a combination therapy, the kit may optionally contain the other therapeutic(s) that makes up the combination.

In certain embodiments, one or more of the components of the kit can be lyophilized and the kit can additionally contain a suitable solvent for reconstitution of the lyophilized components. Individual components of the kit would typically be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration.

In certain embodiments, the reprogramming compound(s) are provided in the kit in the form of pharmaceutical compositions suitable for administration to a subject. In this case, if desired, the container may itself be an inhalant, syringe, pipette, eye dropper, or other such like apparatus, from which the composition may be administered to the subject.

BPTF Reprogramming Compounds

In one aspect, the invention relates to BPTF reprogramming compounds identified by the methods described herein, as well as pharmaceutical compositions and kits comprising these compounds, and uses of these compounds as described above.

Certain embodiments of the invention relate to compounds for reprogramming BPTF having a general formula I:

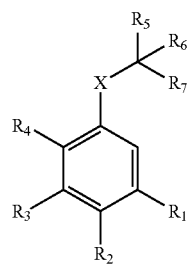

wherein:
(a) X is C=O or S(O)$_2$,
$R_1$ is H, $C_1$-$C_4$ alkyl or $C_1$-$C_4$ alkoxy,
$R_2$ is H, $C_1$-$C_4$ alkyl, $C_1$-$C_4$ alkoxy or halo, and $R_3$ is H, or $R_2$ and $R_3$ taken together with the C atoms they are attached to form:

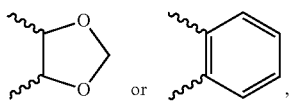

$R_4$ is H, $C_1$-$C_4$ alkyl, $C_1$-$C_4$ alkoxy, or halo,
$R_5$ is H, CH$_2$NMe$_2$ or

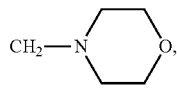

and
$R_6$ is H, and $R_7$ is H, or $R_6$ and $R_7$ taken together form =CH$_2$,
wherein when $R_5$ is H and $R_6$ and $R_7$ taken together form =CH$_2$, X is S(O)$_2$, and wherein when $R_4$ is $C_1$ alkyl, $R_5$ is CH$_2$NMe$_2$, and $R_6$ and $R_7$ taken together form =CH$_2$, then at least one of $R_1$, $R_2$ and $R_3$ is other than H;
or
(b) X is NH,
$R_1$ and $R_2$ are H, $R_3$ and $R_4$ taken together with the C atoms they are attached to form:

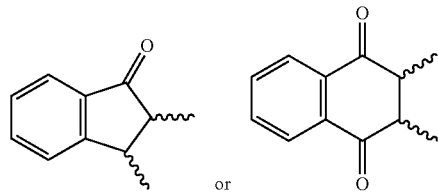

$R_5$ is substituted $C_1$-$C_4$ alkyl or unsubstituted $C_2$-$C_4$ alkyl, wherein each substituent is a halogen, and
$R_6$ and $R_7$ taken together form =O.

Some embodiments of the invention relate to BPTF reprogramming compounds of general Formula I in which:
X is C=O or S(O)$_2$,
$R_1$ is H, $C_1$-$C_4$ alkyl or $C_1$-$C_4$ alkoxy,
$R_2$ is H, $C_1$-$C_4$ alkyl, $C_1$-$C_4$ alkoxy or halo, and $R_3$ is H, or $R_2$ and $R_3$ taken together with the C atoms they are attached to form:

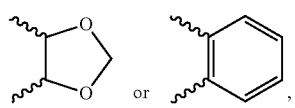

$R_4$ is H, $C_1$-$C_4$ alkyl, $C_1$-$C_4$ alkoxy, or halo,
$R_5$ is H, CH$_2$NMe$_2$ or

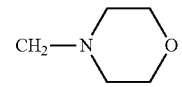

and
$R_6$ is H, and $R_7$ is H, or $R_6$ and $R_7$ taken together form =CH$_2$.

Some embodiments of the invention relate to BPTF reprogramming compounds of general Formula I in which:
X is C=O or S(O)$_2$,
$R_1$ is H or $C_1$-$C_4$ alkyl,
$R_2$ is H, $C_1$-$C_4$ alkyl or halo, and $R_3$ is H, or $R_2$ and $R_3$ taken together with the C atoms they are attached to form:

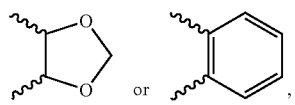

$R_4$ is H, $C_1$-$C_4$ alkyl or halo,
$R_5$ is H, CH$_2$NMe$_2$ or

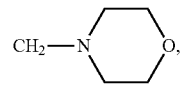

and
$R_6$ is H, and $R_7$ is H, or $R_6$ and $R_7$ taken together form =CH$_2$, wherein when $R_1$, $R_2$, $R_3$ and $R_4$ are each H, then $R_5$ is

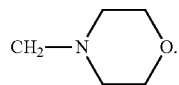

Some embodiments of the invention relate to BPTF reprogramming compounds of general Formula I which have Formula II:

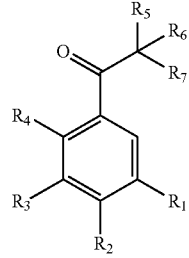

wherein:
$R_1$ is H or $C_1$-$C_4$ alkyl,
$R_2$ is H or halo, and $R_3$ is H, or $R_2$ and $R_3$ taken together with the C atoms they are attached to form:

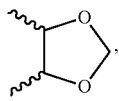

$R_4$ is H, $C_1$-$C_4$ alkyl or halo,
$R_5$ is $CH_2NMe_2$ or

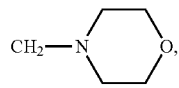

and
$R_6$ is H, and $R_7$ is H, or $R_6$ and $R_7$ taken together form =$CH_2$.

Some embodiments of the invention relate to BPTF reprogramming compounds of general Formula I or II in which each $C_1$-$C_4$ alkyl is Me.

Some embodiments of the invention relate to BPTF reprogramming compounds of general Formula I or II in which:
$R_1$ and $R_4$ are H or Me, and
$R_2$ and $R_3$ are H.

Some embodiments of the invention relate to BPTF reprogramming compounds of general Formula I or II in which:
$R_1$ and $R_3$ are H,
$R_2$ and $R_4$ are H or halo.

Some embodiments of the invention relate to BPTF reprogramming compounds of general Formula I in which:
X is $S(O)_2$,
$R_1$ is H or $C_1$-$C_4$ alkyl,
$R_2$ is H, $C_1$-$C_4$ alkyl or halo, and $R_3$ is H, or $R_2$ and $R_3$ taken together with the C atoms they are attached to form:

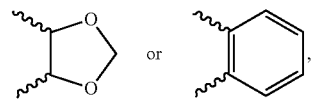

$R_4$ is H, $C_1$-$C_4$ alkyl or halo,
$R_5$ is H, $CH_2NMe_2$ or

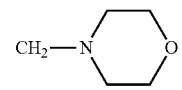

and
$R_6$ is H, and $R_7$ is H, or $R_6$ and $R_7$ taken together form =$CH_2$.

Some embodiments of the invention relate to BPTF reprogramming compounds of general Formula I in which:
X is NH,
$R_1$ and $R_2$ are H,
$R_3$ and $R_4$ taken together with the C atoms they are attached to form:

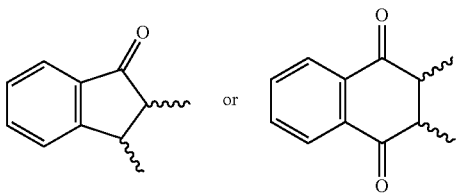

$R_5$ is substituted $C_1$-$C_4$ alkyl or unsubstituted $C_2$-$C_4$ alkyl, wherein each substituent is a halogen, and
$R_6$ and $R_7$ taken together form =O.

Some embodiments of the invention relate to BPTF reprogramming compounds of general Formula I in which:
X is NH,
$R_1$ and $R_2$ are H,
$R_3$ and $R_4$ taken together with the C atoms they are attached to form:

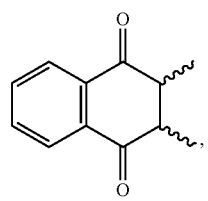

$R_5$ is substituted $C_1$-$C_4$ alkyl or unsubstituted $C_2$-$C_4$ alkyl, wherein each substituent is a halogen, and
$R_6$ and $R_7$ taken together form =O.

Some embodiments of the invention relate to BPTF reprogramming compounds of general Formula I or II as described in any of the foregoing embodiments in which each halo(gen) is Cl.

Some embodiments of the invention relate to BPTF reprogramming compounds of general Formula I that are selected from the group of:

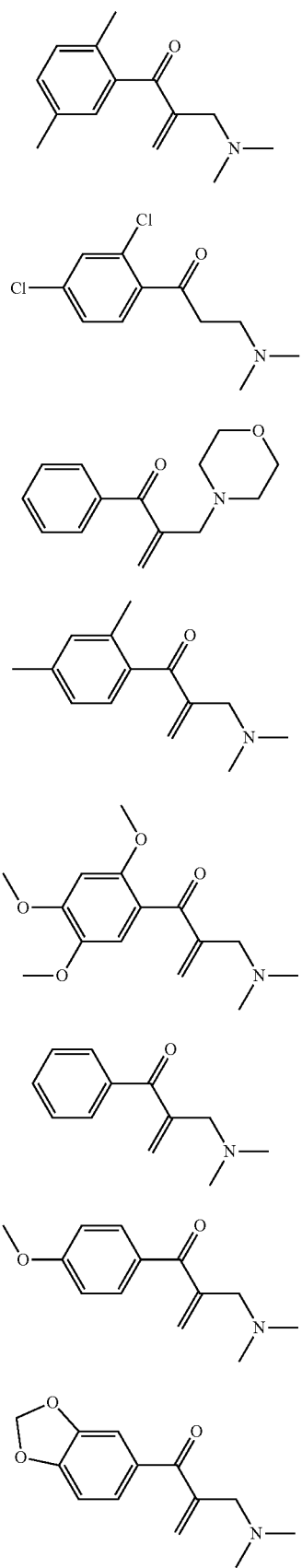
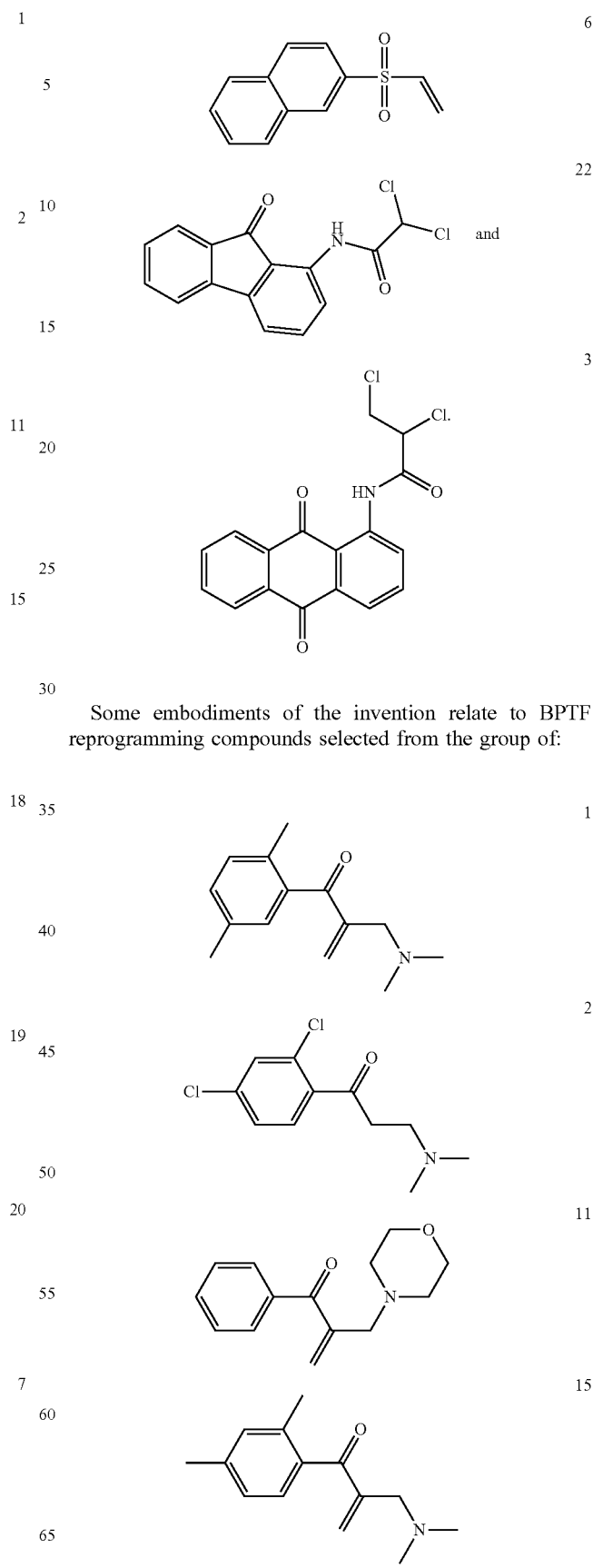
Some embodiments of the invention relate to BPTF reprogramming compounds selected from the group of:

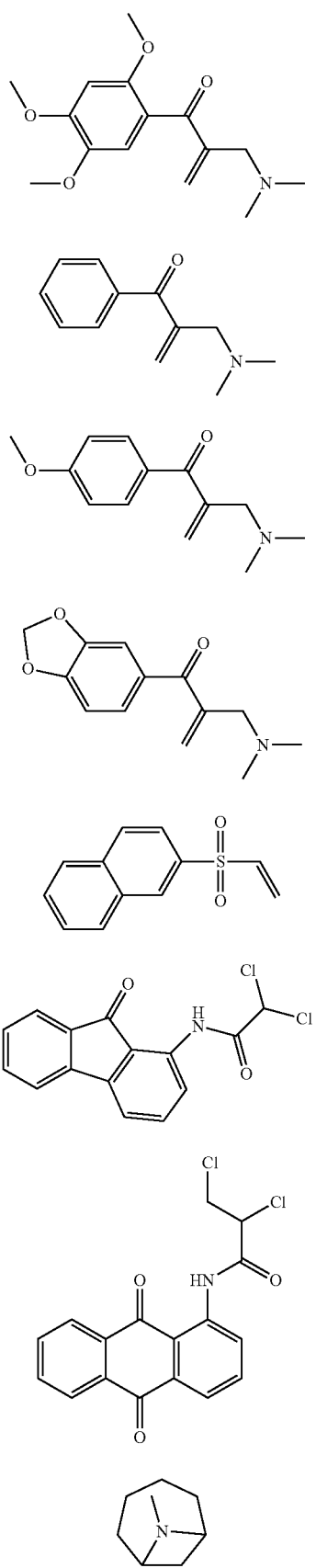
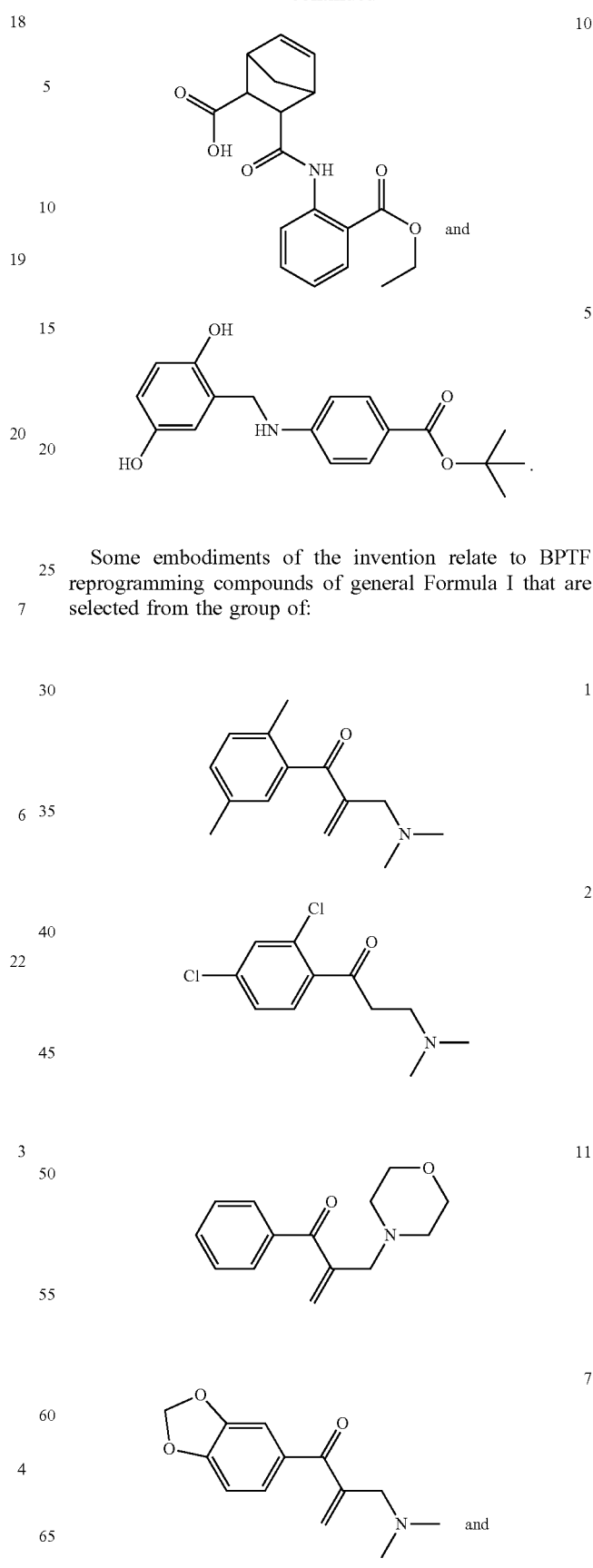
Some embodiments of the invention relate to BPTF reprogramming compounds of general Formula I that are selected from the group of:

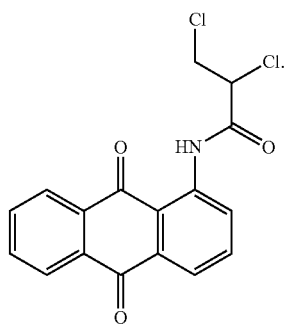
3

Some embodiments of the invention relate to BPTF reprogramming compounds of general Formula I that are selected from the group of:

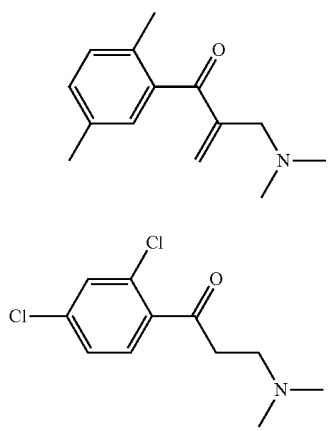

Some embodiments of the invention relate to BPTF reprogramming compounds having the structure:

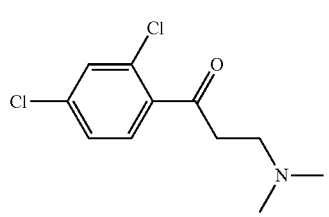

or

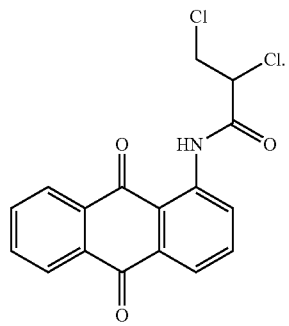
3

CBX2 Reprogramming Compounds

In one aspect, the invention relates to CBX2 reprogramming compounds identified by the methods described herein, as well as pharmaceutical compositions and kits comprising these compounds, and uses of these compounds as described above.

Certain embodiments of the invention relate to compounds for reprogramming CBX2 having general Formula III:

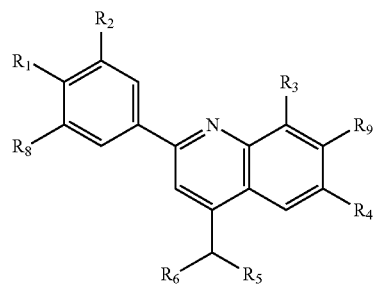

III wherein:
$R_1$, $R_2$, $R_4$ and $R_8$ are each independently H or halo;
$R_3$ is H, halo, $C_1$-$C_4$ alkyl or phenyl, and $R_9$ is H or halo; or $R_3$ and $R_9$ taken together with the C atoms to which they are attached form phenyl;
$R_5$ is $OR_7$ or =O;
$R_6$ is X, $CH_2$ X, $C_1$-$C_4$ alkyl, NH—$NH_2$, $CH_2NR_{10}$,

or piperidinyl;
$R_7$ is H or $C_1$-$C_4$ alkyl;
$R_{10}$ is H, $C_1$-$C_4$ alkyl or $CH_2$-phenyl, and
X is halo.
In some embodiments, in general Formula III:
$R_1$, $R_2$ and $R_4$ are each independently H or halo;
$R_3$ is H, halo, $C_1$-$C_4$ alkyl or phenyl, and $R_9$ is H or halo; or $R_3$ and $R_9$ taken together with the C atoms to which they are attached form phenyl;
$R_5$ is OH or =O;
$R_6$ is X, $CH_2$ X, $C_1$-$C_4$ alkyl, NH—$NH_2$, $CH_2NR_{10}$ or piperidinyl;
$R_8$ is H;
$R_{10}$ is $C_2$-$C_3$ alkyl or $CH_2$-phenyl, and
X is halo.

In some embodiments, in Formula III:
$R_1$, $R_2$ and $R_4$ are each independently H or halo;
$R_3$ is H, halo, $C_1$-$C_4$ alkyl or phenyl, and $R_9$ is H or halo; or $R_3$ and $R_9$ taken together with the C atoms to which they are attached form phenyl;
$R_5$ is OH or =O;
$R_6$ is $CH_2$X or piperidinyl;
$R_8$ is H;
$R_{10}$ is $C_2$-$C_3$ alkyl or $CH_2$-phenyl, and
X is halo.

In some embodiments, compounds of general Formula III have Formula IV:

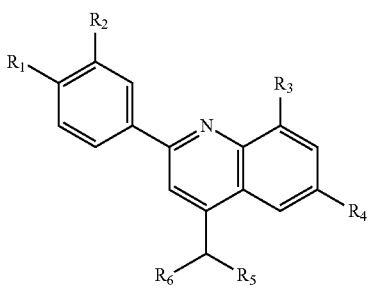

IV wherein:
$R_1$, $R_2$ and $R_4$ are each independently H or halo;
$R_3$ is H, halo or phenyl;
$R_5$ is OH or =O;
$R_6$ is X, $CH_2$X or $C_1$-$C_4$ alkyl, and
X is halo.

In some embodiments, in Formula IV:
$R_1$, $R_2$ and $R_4$ are each independently H or halo;
$R_3$ is H, halo or phenyl;
$R_5$ is =O;
$R_6$ is $CH_2$X, and
X is halo.

In some embodiments, compounds of general Formula III have Formula V:

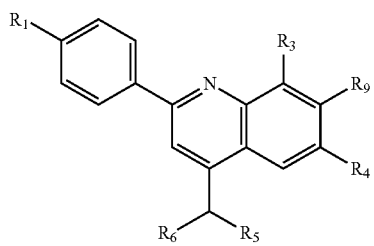

V wherein:
$R_1$ and $R_4$ are each independently H or halo;
$R_3$ is H, halo or $C_1$-$C_4$ alkyl, and $R_9$ is H or halo; or $R_3$ and $R_9$ taken together with the C atoms to which they are attached form phenyl;
$R_5$ is OH or =O;
$R_6$ is NH—$NH_2$, $CH_2NR_{10}$, or piperidinyl;
$R_{10}$ is $C_2$-$C_3$ alkyl or $CH_2$-phenyl.

In some embodiments, in Formula V:
$R_1$ and $R_4$ are each independently H or halo;
$R_3$ is H, halo or $C_1$-$C_4$ alkyl, and $R_9$ is H or halo; or $R_3$ and $R_9$ taken together with the C atoms to which they are attached form phenyl;

$R_5$ is OH;
$R_6$ is piperidinyl;
$R_{10}$ is $C_2$-$C_3$ alkyl or $CH_2$-phenyl.

In certain embodiments of the invention in compounds of Formula III, IV or V, each halo is Cl or Br.

In some embodiments in compounds of Formula III or V, X is Br.

In some embodiments of the invention, compounds of general Formula III have the following structures:

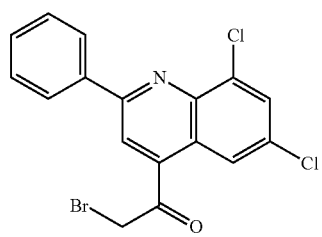

50

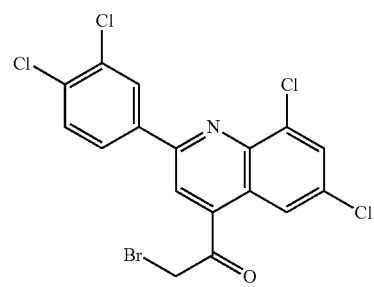

52

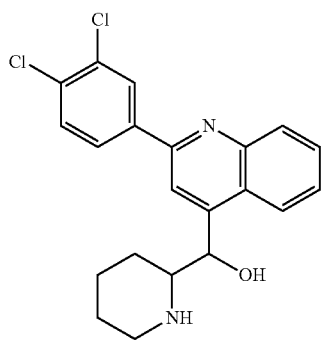

51

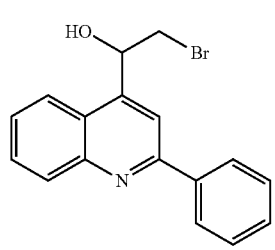

25

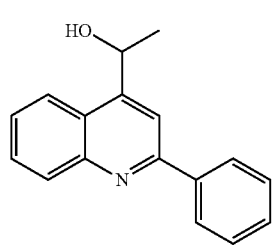

26

-continued
| | |
|---|---|
| 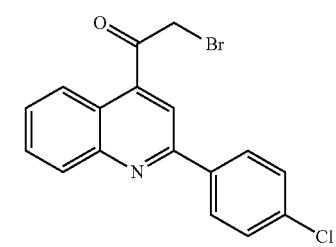 27 | 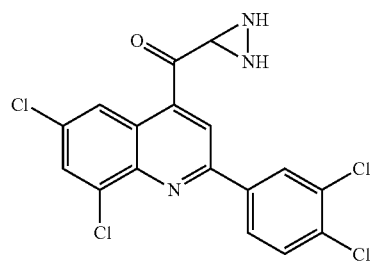 33 |
| 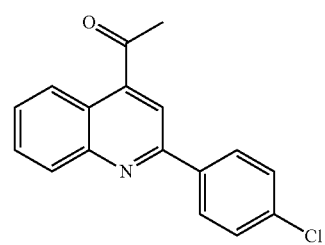 28 | 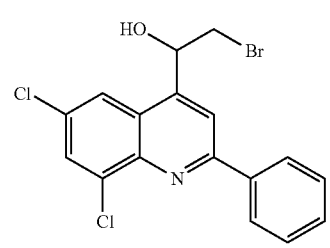 34 |
| 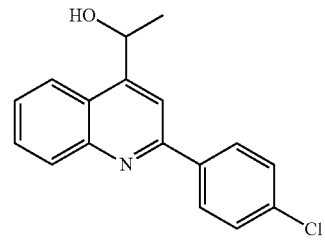 29 | 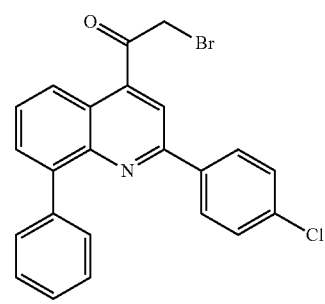 35 |
| 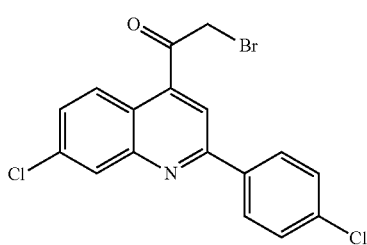 30 | 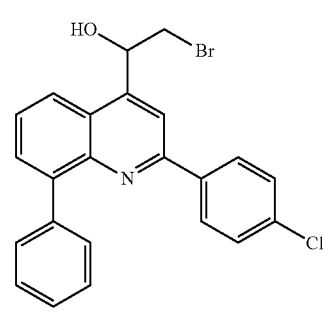 36 |
| 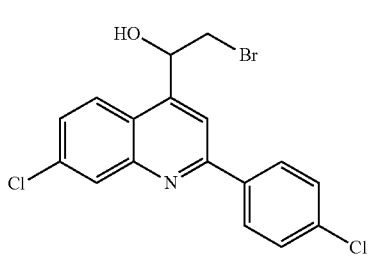 31 | 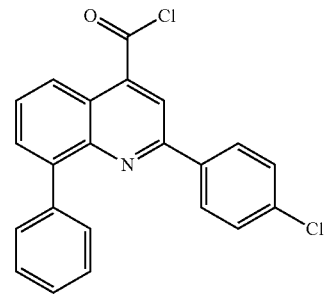 37 |
| 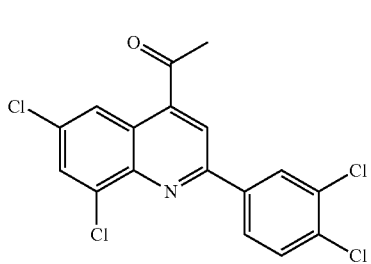 32 | |

38
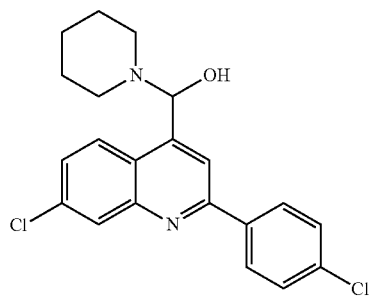
39
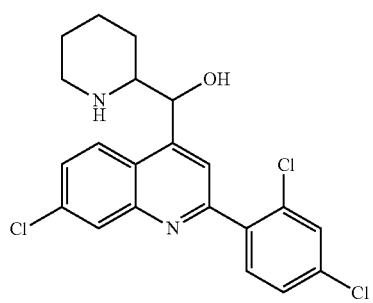
40
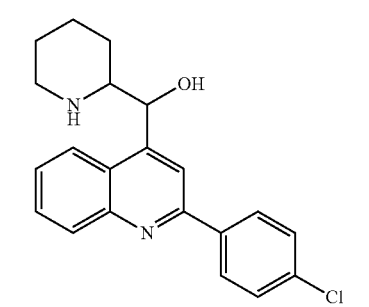
41
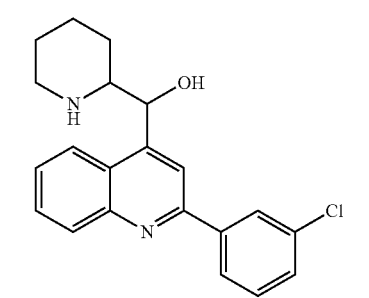
42
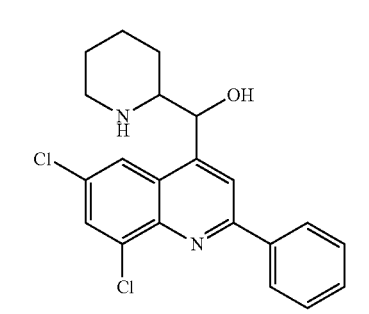
43
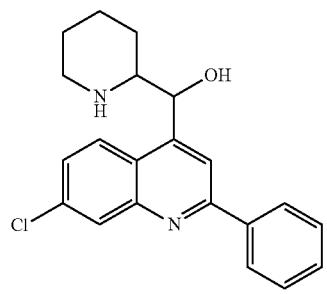
44
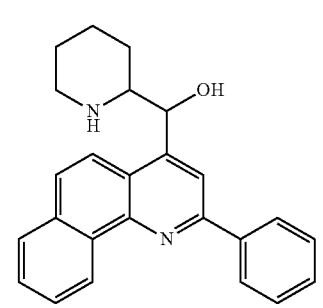
45
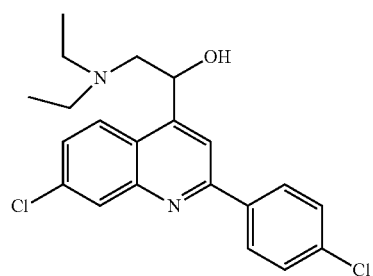
46
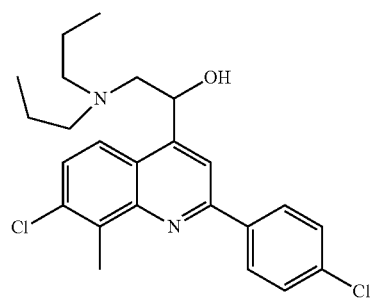
47
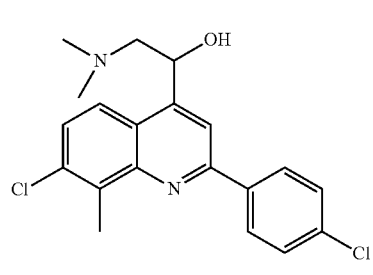

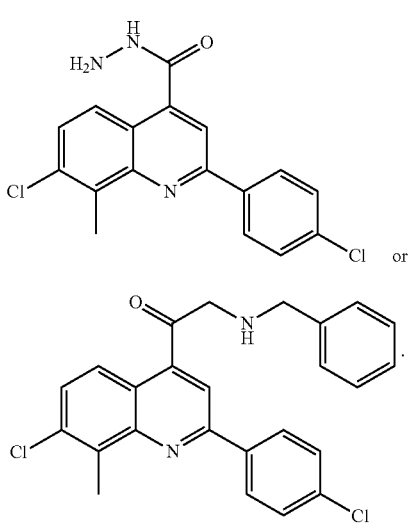

The BPTF and CBX2 reprogramming compounds described above can be obtained/sourced from various repositories, for example, from the NCI Developmental Therapeutics Program (DTP) open chemical repository at the National Cancer Institute (NCI)/National Institute of Health (NIH).

In certain embodiments, compounds of Formulae I, II, III, IV and V may possess a sufficiently acidic group, a sufficiently basic group, or both functional groups, and accordingly react with a number of organic and inorganic bases, or organic and inorganic acids, to form pharmaceutically acceptable salts. The term "pharmaceutically acceptable salt" as used herein, refers to a salt of a compound that is substantially non-toxic to living organisms. Typical pharmaceutically acceptable salts include those salts prepared by reaction of a compound of Formulae I, II, III, IV or V with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napththalene-2-sulfonate, mandelate and the like. Pharmaceutically acceptable acid addition salts of particular interest are those formed with mineral acids such as hydrochloric acid and hydrobromic acid, and those formed with organic acids such as maleic acid and methanesulphonic acid.

Salts of amine groups may also comprise quarternary ammonium salts in which the amino nitrogen carries a suitable organic group such as an alkyl, lower alkenyl, substituted lower alkenyl, lower alkynyl, substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing pharmaceutically acceptable salts thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counterion forming a part of a pharmaceutically acceptable salt is usually not of a critical nature, so long as the salt as a whole is pharmacologically acceptable and as long as the counterion does not contribute undesired qualities to the salt as a whole.

In some embodiments, the present invention further encompasses pharmaceutically acceptable solvates of a compound of Formulae I, II, III, IV or V. Many of the compounds of Formulae I, II, III, IV and V can combine with solvents such as water, methanol, ethanol and acetonitrile to form pharmaceutically acceptable solvates such as the corresponding hydrate, methanolate, ethanolate and acetonitrilate.

Certain compounds of Formulae I, II, III, IV or V may have one or more asymmetric (chiral) centres and/or one or more unsaturated bonds. As a consequence, these compounds can be present as racemates, individual enantiomers, mixtures of enantiomers, individual diastereomers, mixtures of diastereomers, individual isomers and mixtures of isomers. Certain embodiments of the invention provide compounds of Formulae I, II, III, IV or V in an enantiomeric, diastereomeric or isomeric form, or as mixtures of enantiomers, diastereomers or isomers.

In certain embodiments, the invention provides for prodrugs of the compounds of Formulae I, II, III, IV or V. The term "prodrug" as used herein refers to compound that has undergone a chemical derivation such as substitution or addition of a further chemical group to change (for pharmaceutical use) one or more of its physico-chemical properties, and that yields the active compound per se by one or a series of metabolic transformations after administration to a subject. Physico-chemical properties that may be changed by conversion of the compound into a prodrug form include, for example, solubility, bioavailability, absorption, distribution, site specificity, stability, release characteristics, toxicity, and the like. Examples of chemical derivatives of compounds of Formulae I, II, III, IV and V that may be prepared in order to convert the compound into a prodrug include, but are not limited to, ester derivatives, ether derivatives, carbamate derivatives, amide derivatives, imine derivatives, and derivatization with an appropriate carrier moiety directly or via a linker group. Examples of prodrugs and methods of producing a prodrug of a given acting compound are well known to those skilled in the art and can be found, for example, in Krogsgaard-Larsen et al. (*Textbook of Drug Design and Discovery*, Taylor & Francis, New York, N.Y. (April 2002)).

The preparation of salts, solvates and prodrugs can be carried out by methods known in the art. It will be appreciated that non-pharmaceutically acceptable salts, solvates or prodrugs also fall within the scope of the invention since those may be useful in the preparation of pharmaceutically acceptable salts, solvates or prodrugs.

To gain a better understanding of the invention described herein, the following examples are set forth. It will be understood that these examples are intended to describe illustrative embodiments of the invention and are not intended to limit the scope of the invention in any way.

EXAMPLES

Example 1

Small Molecule Reprogramming of BPTF

Molecular Modeling.

Molecular dynamic simulations (MD), carried out with GROMACS-4.0.5 package together with software for chemical structures search implemented at www.pubchem.org, were the main modeling tool in this study. Molecular docking methods using the ICM package (Molsoft LLC, San Diego, Calif.), showed poor accuracy and generally unsatisfactory results.

The 3D model of the BPTF protein complexed with the H3K4 N-terminal tail peptide from Li, H., et al (2006, *Nature*, 442:91-95) was used (protein databank accession code 2FUU). Prior to the simulations, the model was placed in triclinic box of simple point charge (SPC) water (Berendsen, H. et al. *Intermolecular Forces* 1981, 331-342) to which 100 mM NaCl equivalent was added including neutralizing counterions. Periodic boundaries were applied in all directions. The N- and C-termini of all protein molecules were ionized. To all other amino acids were assigned their canonical state at physiological pH. Energy terms from the GROMOS96 43a1 parameter set (Scott, W. et al. *J Phys Chem A* 1999, 103, 3596-3607) were applied to all molecular species in the system. To handle two $Zn^{2+}$ ions, the parameters set was updated with eight new coordinate chemical bonds (and corresponding angles): for the first zinc atom to SG atom of C11, SG atom of C13, ND1 atom of H34 and SG atom of C37; for the second zinc atom to SG atom of C26, SG atom of C29, SG atom of C53 and SG atom of C56. The charge distribution on corresponding resides was updated either: for the first $Zn^{2+}$ coordination complex one electron was smoothed along the H34 imidazole ring and the second was divided equally between the zinc atom and three sulfur atoms of Cys residues; for the second zinc atom, charge was set as −0.4 e and the remains of two electrons were equally divided among four sulfur atoms of Cys residues.

The K4me3 residue of the histone peptide was edited to replace two of the three methyl groups with hydrogen atoms. Due to the absence of accurate parameters for cation-π interactions in GROMOS96 force field, all atoms of aromatic rings, but not those of the Y17 residue, in the BPTF aromatic cage, as well as the NZ atom of mono-methylated Lys 4 were frozen at their coordinates in the 2FUU structure with 1000 $kJ·mol^{-1}·nm^{-2}$ as hard harmonic position restrains.

The conformation of the Y17 sidechain was manually edited with rotations around dihedral angles so the hydroxyphenyl ring no longer occupied the cavity occupied in the original model, but was located at the opposite side of the site relative to the Y17 CA atom. The empty cavity was then used as a docking site for small organic compounds in the initial configuration of triple complex models. All complexes were constructed manually by rotation, translation and dihedral angle alternations of compounds which were optimized in a vacuum at the PRODRG server (Schuttelkopf, A. W. et al, *Acta Crystallogr. D Biol. Crystallogr.* 2004, 60:1355-1363). Due to some lack of accuracy in parameter sets generated by PRODRG (Lemkul, J. A. et al. *J. Chem. Inf. Model.* 2010, 50:2221-2235), the non-bonded parameters of compounds were intensively edited manually, in particular, charge distribution was rewritten for each compound.

All MD calculations were carried out with somewhat straightened non-bonded interactions: both Leonard-Jones and Coulomb short range interactions were switched at 1.3 nm and vanished at 1.4 nm with neighbor-searching radii set to 1.5 nm and repeated each 10 steps of MD integrator. Long-range electrostatic interactions were modeled with the particle mesh Ewald (PME) algorithm (Essmann, U. et al. *J. Chem. Phys.* 1995, 103:8577-8593). To model solvated complexes, the structures were relaxed by 1-bfgs minimization (Liu, D. C. and Nocedal, *J. Math. Program.* 1989, 45:503-528) and 50 ps of molecular dynamic simulations with restrained positions of heavy atoms of both the protein and the compound simulated under a constant volume (NVT) ensemble. A simulated annealing (Kirkpatrick, S. et al. *Science* 1983, 220:671-680, Cerny V. J. *Optimiz. Theory Appl.* 1985, 45:41-51) was used to warm up the system from initial velocities assigned according to Boltzmann distribution at T=10K to T=310K. Following NVT warm up, 100 ps of constant pressure (NPT) equilibration was performed. Complex and other atoms were coupled to separate temperature coupling baths and the temperature was maintained at T=310K. For equilibration, weak couplings (Berendsen, H. J. C. et al. *J. Chem. Phys.* 1984, 81:3684-3690) were used to maintain pressure isotropically at 1.0 bar and the Berendsen weak coupling method (Berendsen, 1984, ibid.) was used to maintain constant temperature. All subsequent productive runs were performed with the more accurate Nose-Hoover thermostat (Nose, S. *Mol. Phys.* 2002, 100:191-198, Hoover, W. *Physical Review A* 1985, 31:1695-1697) with a temperature coupling time constant of 0.1 ps and the Parrinello-Rahman barostat (Parrinello, M. et al. *J. Appl. Phys.* 1981, 52:7182-7190, Nose, S. and Klein, M. L. *Mol. Phys.* 1983, 50:1055-1076) with a pressure coupling time constant of 1.0 ps under NPT ensemble. This combination of thermostat and barostat ensured that a true NPT ensemble was sampled and only small artifacts, if any, resulted from the restraining of a tiny (22 atoms) and compact aromatic cage. For visual inspections of MD trajectories, VMD viewer (Humphrey, W.; et al. *J. Mol. Graph.* 1996, 14:33-8, 27-8) was used.

Results and Discussion:

Loss of function (LoF) mutations in MLL2 are predicted to result in loss of H3K4me2 and H3K4me3 epigenetic marks because MLL is the only effector protein for these marks. As methylation of H3K4 is a well-known activation mark, the oncogenic functions of MLL2 inactivation may result in protection of a cancer cell from expression of genes normally activated with the H3K4 methyl mark.

The reader of the H3K4me2 and me3 marks is the BPTF protein. BPTF binds to the me2 and me3 marks, but does not bind to the H3K4me0,1 marks (Li H., et al., 2007, *Mol. Cell.*, 28:677-691). H3K4me0,1 marks are bound by the L3MBTL protein (Li H., et al., ibid.). It is shown herein that it is possible to design a chemical compound that reprograms BPTF to bind to H3K4me0,1 marks with higher affinity than normal and in such a way simulate MLL2 activity. The reprogramming is accomplished by forming a triple complex of BPTF, the H3K4me0 or me1 tail and a small molecule compound so that the latter creates an environment favourable for BPTF binding to H4K4me0 and/or me1.

An intensive computational protocol was used to identify promising candidates that would reprogram BPTF to demonstrate an affinity for H3K4me0,1. BPTF recognizes the tri-methylated lysine via an aromatic cage formed by 4 aromatic residues: W32, Y10, Y23 and Y17. The cage forms a box in 3D space, of which 4 faces are created by these aromatic residues, one face is where the K4 backbone is found and the last face is open to water. Without any hydrogen bonding motifs present within the cage, the cage selectively binds tri-methylated lysines, which have no hydrogen atoms at the NZ atom. To reprogram the specificity of BPTF, it is necessary to anchor a compound within or proximal to the active site that provides a hydrogen bonding motif to allow formation of a triple complex with H3K4me0,1.

The approach taken was to deconstruct one of the faces of the aromatic cage to provide both a site for compound anchoring and access to the active site to supply a hydrogen acceptor motif.

A model of the BPTF-H3K4me1 tail peptide complex was taken from Li, H., et al (2006, *Nature*, 442:91-95). The model was simulated with molecular dynamics (MD) for 2 ns using position restraints applied to the aromatic cage of BPTF (side-chains of residues W32, Y10 and Y23) and the NZ atom of K4 of the histone tail peptide. The least conserved residue of the aromatic cage, Y17, was selected for deconstruction.

A probe of virtual compounds (Table 1) was used to substitute Y17 in the active site of BPTF. Two independent runs with compounds V1 and V2 were used initially with the triple complex being simulated for 6 ns MD. As the probe dissociated, failing to compete with Y17, a region of the compounds responsible for failure was identified by reviewing the MD trajectory, and this region was mutated. In such way, the evolution of the probe compounds was:

V1→V11→V12→V13→V14→V3←V23←V22←V21←V2

The final virtual probe V3 provided a stable complex during the 6 ns MD. V3 was able to out-compete Y17 for the face of the aromatic cage and to form two good hydrogen bonds between the ketone oxygen and the two hydrogen atoms of K4(H2+,me1).

TABLE 1

Structures of Probe Compounds

| Structure | Name (Probe number) |
|---|---|
| 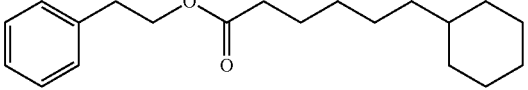 | 6-cyclohexyl-hexanoicacid phenethyl ester (V1) |
| 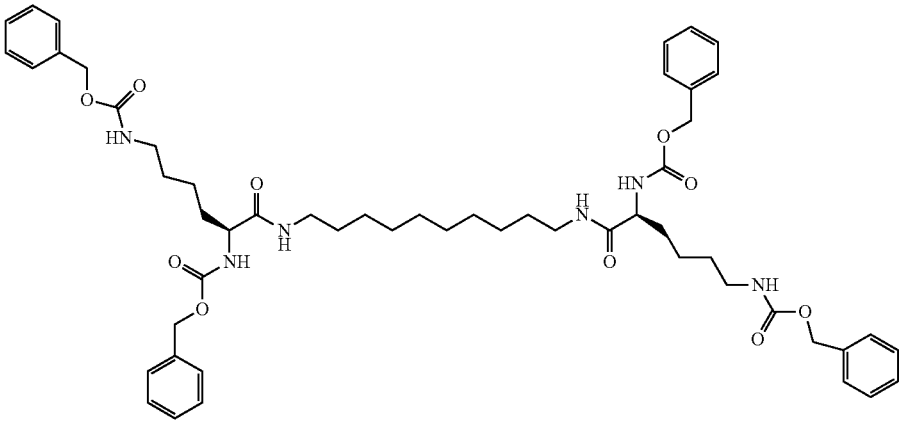 [SMILES: O=C(NCCCC[C@H](NC(=O)OCc1ccccc1)C(=O)NCCCCCCCCCCNC(=O)[C@H](CCCCNC(=O)OCc1ccccc1)NC(=O)OCc1ccccc1)OCc1ccccc1] | {5-benzyloxyxarbonyl-amino-1-[10-(2,6-bis-benzyloxycarbonyl-amino0hexanoylamino)-decylcarbamoyl]-pentyl}-carbamic acid benzyl ester (V2) |
| 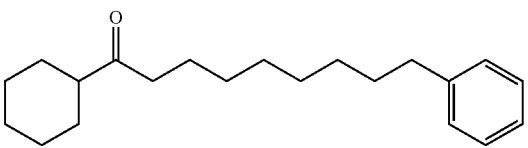 [SMILES: O=C(CCCCCCCCc1ccccc1)C1CCCCC1] | 1-cyclohexyl-9-phenyl-nonan-1-one (V11) |
| 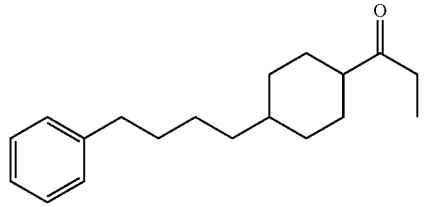 [SMILES: CCC(=O)C1CCC(CCCCc2ccccc2)CC1] | 1-[4-(4-phenyl-butyl)-cyclohexyl]-propan-1-one (V12) |

TABLE 1-continued

Structures of Probe Compounds

| Structure | Name (Probe number) |
|---|---|
| 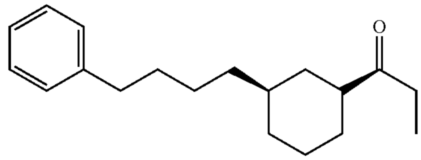 | 1-[3-(5-phenyl-butyl)-cyclohexyl]-propan-1-one (V13) |
| 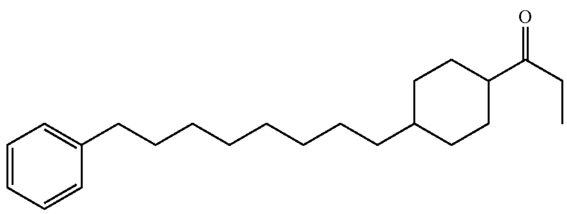 [SMILES: CCC(=O)C1CCC(CCCCCCCCc2ccccc2)CC1] | 1-[4-(8-phenyl-octyl)-cyclohexyl]-propan-1-one (V14) |
| 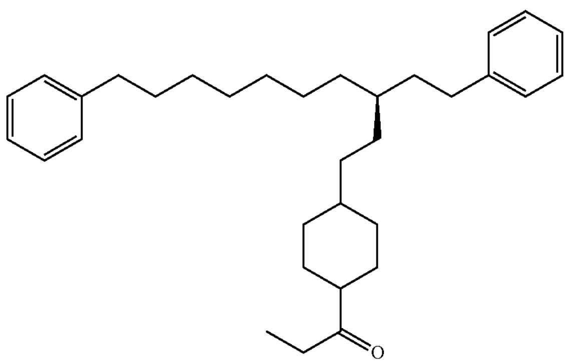 [SMILES: CCC(=O)C1CCC(CC[C@@H](CCCCCCCc2ccccc2)CCc2ccccc2)CC1] | 1-[4-(3-phenethyl-10phenyl-decyl)-cyclohexyl]-propan-1-one (V22) |
| 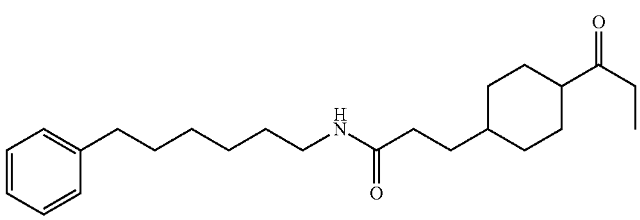 [SMILES: CCC(=O)C1CCC(CCC(=O)NCCCCCCc2ccccc2)CC1] | N-(6-phenyl-hexyl)-3-(4-propionyl-cyclohexyl)-propionamide (V23) |
| 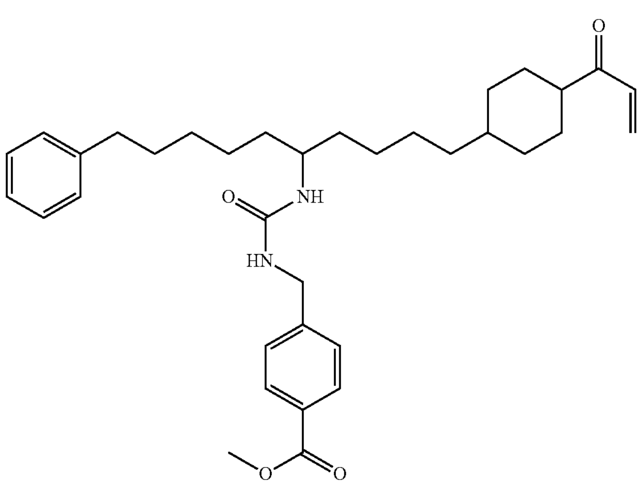 [SMILES: C=CC(=O)C1CCC(CCCCC(CCCCCc2ccccc2)NC(=O)NCc2ccc(C(=O)OC)cc2)CC1] | 4-(3-{1-[4-(4-acryloyl-cyclohexyl)-butyl]-6-phenyl-hexyl}-ureisomethyl)-benzoic acid methyl ester (V21) |

TABLE 1-continued

Structures of Probe Compounds

| Structure | Name (Probe number) |
|---|---|
| 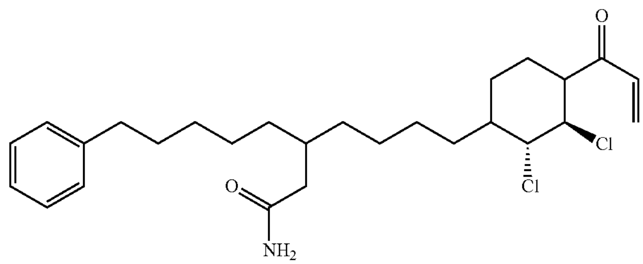 [SMILES: C=CC(=O)C1CCC(CCCCC(CCCCCc2ccccc2)CC(N)=O)[C@@H](Cl)[C@@H]1Cl] | 3-[4-(4-acryloyl-2,3-dichloro-cyclohexyl)-butyl]-8-phenyl-octanoic acid amide (V3) |

The average protein structure from the final complex with the V3 probe was then used to select real compounds as potential BPTF reprogramming compounds by docking compounds from the National Cancer Institute (NCI) library. After manual reviewing of approximately 5 000 top-scored complexes of compounds from NCI library, 22 candidate structures that provided stable 6 ns MD of the triple complex were selected. During selection, the fact that GROMOS96 force field has no special cation-π parameters was accounted for such that if a probe having an aliphatic ring was found to be stable during the simulation, structures in which this anchoring ring was aromatic were selected as preferred structures.

The selected set of compounds was tested in vitro for activity in the SU-DHL-9 cell line (homozygous LoF MLL2 mutant) using the protocol outlined in Example 3. Further optimization based on similarity of active compounds resulted in identification of a set of compounds (NSC382001 (Compound 1), NSC304107 (Compound 2) and NSC127763 (Compound 3)) active against the MLL2 double LoF mutant cell line, but inactive against wild-type cells (see Table 2). A model showing the "triple reprogramming complex" of Compound 2, BPTF and the H3K4me1 peptide is shown in FIG. 1.

Other compounds that were identified and demonstrated an ability in vitro to selectively kill the cell-lines SU-DHL-9 and Pfeiffer, which possess MLL2 LoF homozygous mutations, are also shown in Table 2. These compounds showed activity in these tests at a concentration of approximately 1 M.

TABLE 2

Candidate BPTF Re-Programming Compounds

| Compound | Structure | Name (NSC number) |
|---|---|---|
| 1 | 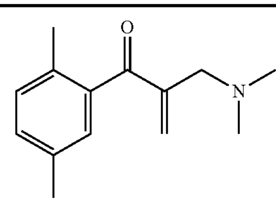 | 2-dimethylaminomethyl-1-(2,5-dimethyl-phenyl)-propenone (NSC382001) |
| 2 | 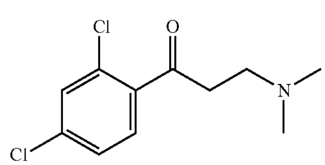 | 1-(2,4-dichloro-phenyl)-3-dimethylamino-propan-1one (NSC304107) |
| 3 | 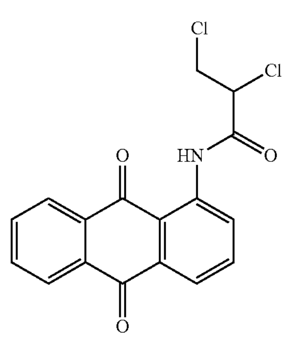 [SMILES: O=C1c2ccccc2C(=O)c2c(NC(=O)C(Cl)CCl)cccc21] | 2,3-didhloro-N-(9,10-dioxo-9,10-dihydro-anthracen-1-yl)-propionamide (NSC127763) |

TABLE 2-continued

Candidate BPTF Re-Programming Compounds

| Compound | Structure | Name (NSC number) |
|---|---|---|
| 4 | 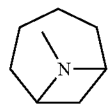 | 7-methyl-7-aza-bicyclo[4.1.1]octane (NSC79037) |
| 5 | 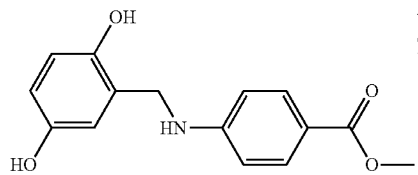 | tert-butyl 4-[(2,5-dihydroxyphenyl)methylamino]benzoate (NSC677696) |
| 6 | 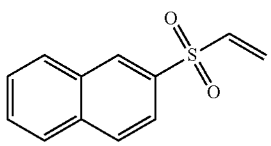 | 2-ethenylsulfonylnaphthalene (NSC202577) |
| 7 | 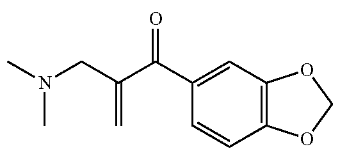 [SMILES: C=C(CN(C)C)C(=O)c1ccc2c(c1)OCO2] | 1-(1,3-benzodioxol-5-yl)-2-[(dimethylamino)methyl]prop-2-en-1-one (NSC382006) |
| 8 | 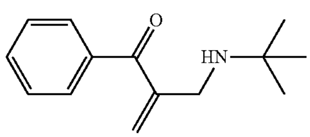 | 2-[(tert-butylamino)methyl]-1-phenylprop-2-en-1-one (NSC313429) |
| 9 | 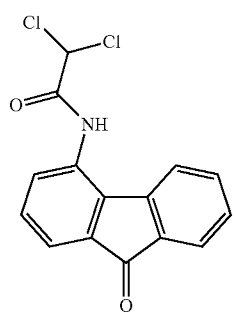 [SMILES: O=C1c2ccccc2-c2c(NC(=O)C(Cl)Cl)cccc21] | 2,2-dichloro-N-(9-oxofluoren-4-yl)acetamide (NSC74980) |
| 10 | 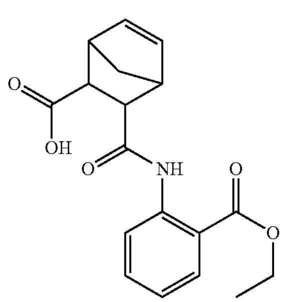 [SMILES: CCOC(=O)c1ccccc1NC(=O)C1C2C=CC(C2)C1C(=O)O] | 2-[(2-ethoxycarbonylphenyl)carbamoyl]bicyclo[2.2.1]hept-5-ene-3-carboxylic acid (NSC270155) |
| 11 | 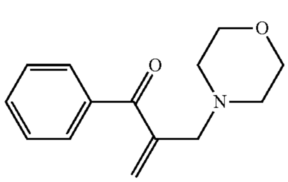 [SMILES: C=C(CN1CCOCC1)C(=O)c1ccccc1] | 2-(morpholin-4-ylmethyl)-1-phenylprop-2-en-1-one (NSC372471) |

Example 2

Identification, Testing and Analysis of Additional BPTF Reprogramming Compounds The initial screen of candidate BPTF reprogramming compounds (see Example 1) resulted in the identification of two promising scaffolds (A and B, below) which were further optimized manually using a Structure-Activity Relationship (SAR) approach (see FIG. 1) leading to the identification of additional candidate BPTF reprogramming compounds as shown in Tables 3 and 4. These compounds were tested for activity in vitro in the SU-DHL-9 and Pfeiffer cell lines using the protocol outlined in Example 3. The activity of the most active compounds was around 2 µM for the SU-DHL-9 cell line and around 6 µM for the Pfeiffer cell line, while no cytotoxicity is observed against negative controls at 10 µM.

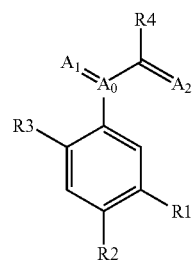

Scaffold a

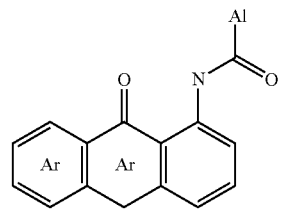

Scaffold b

TABLE 3

| Compound | Structure | NSC Number | % Cell Proliferation |
|---|---|---|---|
| 1 | 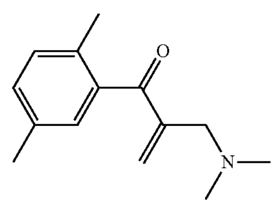 [SMILES: C=C(CN(C)C)C(=O)c1cc(C)ccc1C] | 382001 | <10 |
| 12 | 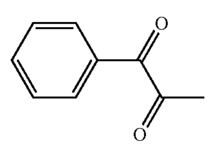 | 685405 | 105 |
| 13 | 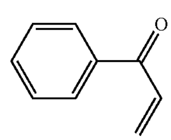 | 174109 | 137 |
| 8 | 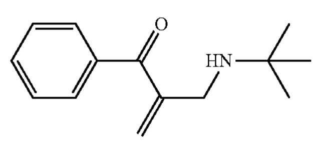 [SMILES: C=C(CNC(C)(C)C)C(=O)c1ccccc1] | 313429 | 92 |
| 14 | 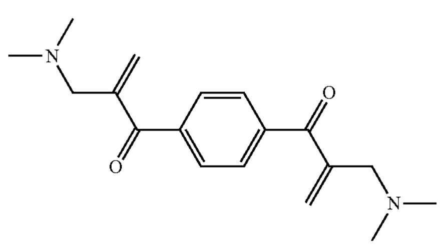 | 382008 | 93 |

Candidate BPTF Reprogramming Compounds Based on Scaffold A

TABLE 3-continued

Candidate BPTF Reprogramming Compounds Based on Scaffold A

| Compound | Structure | NSC Number | % Cell Proliferation |
|---|---|---|---|
| 2 | 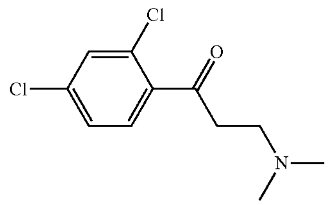 | 304107 | <10 |
| 11 | 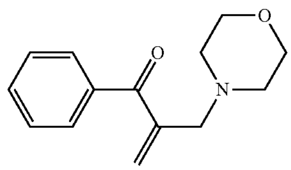 [SMILES: C=C(CN1CCOCC1)C(=O)c1ccccc1] | 372471 | 26 |
| 15 | 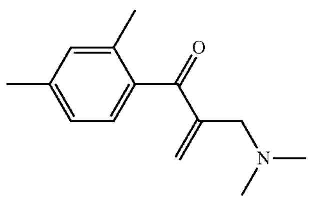 | 382000 | 61 |
| 16 | 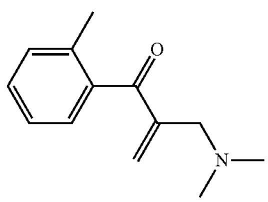 | 382002 | 107 |
| 17 | 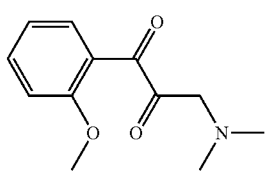 [SMILES: COc1ccccc1C(=O)C(=O)CN(C)C] | 382003 | 89 |
| 18 | 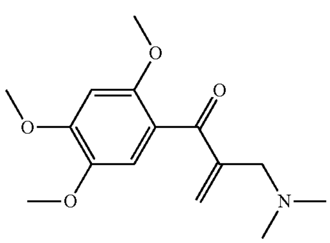 | 382005 | 80 |
| 19 | 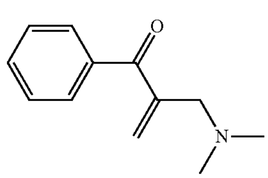 | 382011 | 77 |

TABLE 3-continued
Candidate BPTF Reprogramming Compounds Based on Scaffold A
| Compound | Structure | NSC Number | % Cell Proliferation |
|---|---|---|---|
| 20 | 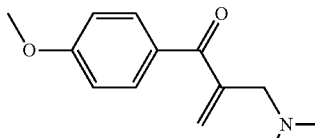 | 603553 | 83 |
| 7 | 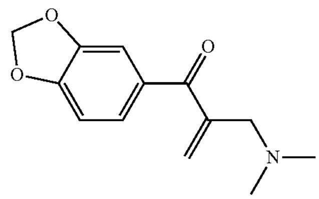 [SMILES: C=C(CN(C)C)C(=O)c1ccc2c(c1)OCO2] | 382006 | 29 |
| 6 | 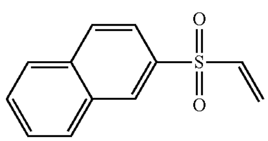 | 202577 | 69 |
| 21 | 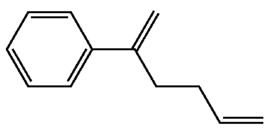 | 54367 | 105 |
TABLE 4
Candidate BPTF Reprogramming Compounds Based on Scaffold B
| Compound | Structure | NSC Number | % Cell Proliferation |
|---|---|---|---|
| 22 | 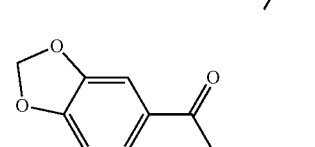 | 123818 | 86 |
| 9 | 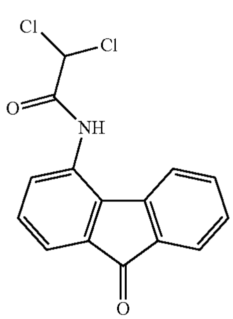 [SMILES: O=C1c2ccccc2-c2c(NC(=O)C(Cl)Cl)cccc21] | 74980 | 117 |
| 23 | 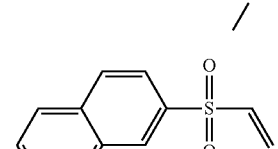 | 134391 | 114 |
| 3 | 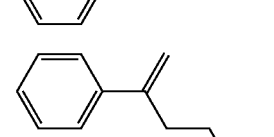 | 127763 | <10 |

TABLE 4-continued

Candidate BPTF Reprogramming Compounds Based on Scaffold B

| Compound | Structure | NSC Number | % Cell Proliferation |
|---|---|---|---|
| 24 | (1-acetamido-anthraquinone structure) | 30421 | 107 |

Structure-Activity Relationship (SAR):

For both active scaffolds, SAR analysis (selective toxicity against SU-DHL-9, Tables 2 and 3) is generally in agreement with a molecular model of a triple complex. According to the MD model (FIG. 1) for scaffold A, R1, R2, R3 and R4 should be hydrophobic and, all except R4, which stabilizes Y17 at a different position, should be reasonably small with a minimum amount of rotatable bonds in order to fit the hydroxyphenyl binding site. Comparison of active Compounds 1 and 2 with inactive or minimally active Compounds 16, 17 and 19 confirm that a small hydrophobic R1 and R3 has a negative effect on activity which can be only slightly compensated for by R2 substitution—as can be seen from the activity of Compounds 15 and 20. Compound 18 with small but rotatable methoxy groups at positions R1, R2 and R3 has only modest activity, but if the methoxy rotations are significantly restrained in a dioxol ring, the activity is restored as can be seen from Compound 7. R4 exerts a more complex effect and can fully compensate for a lack of R1, R2 and R3 (as in Compound 11) or have no effect as in Compound 8. A potential explanation for this complexity may be competition with the Y17 sidechain, with the methyl-piperidine tail being able to stabilize outside the cavity while t-butyl-methyl-amine cannot.

Absence of any substitution at R1, R2, R3 and R4 has a strongly negative effect in activity as expected (see Compound 13). Compound 14 with symmetrical substitution also lacks activity, probably arguing in favor of a small size of R2 being desirable.

A crucial effect of reprogramming motif A1 is confirmed by Compound 21, which lacks a carbonyl group at this position. A much lower importance of the A0 motif is shown by Compound 6, although an absence of R4 in this compound results in only moderate activity. A2 appears not to be critical as expected (compare compound pairs Compound 1/Compound 2 and Compound 17/Compound 19).

Similar SAR conclusions can be made for scaffold B. Although the NCI library contains relatively few compounds that are structural homologues of active Compound 3 (NCI127763), the importance of a long hydrophobic R4 analogue is confined by comparison of Compound 3 and the partially active Compound 22 with the inactive Compounds 23 (R4 hydrophobicity) and 24 (R4 length). A crucial effect of the intermolecular reprogramming hydrogen bond is confirmed by the Compound 3/Compound 9 pair.

In accordance with the spatial model, the results can be interpreted as the aromatic part of the molecule occupying the Y17 binding pocket, with the amide oxygen reprogramming BPTF and the aliphatic tail stabilizing a new position of the Y17 sidechain.

Example 3

In Vitro Activity of Compounds 1-3

Figure 2:
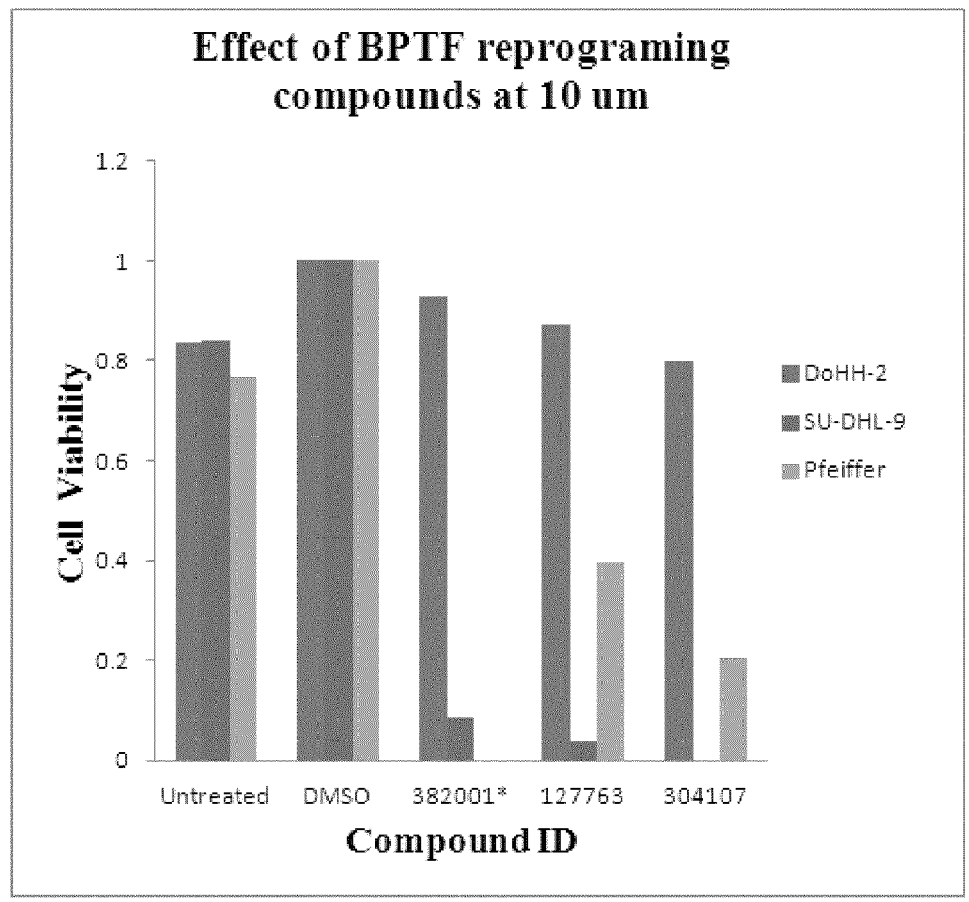
FIG. 2 presents the results of experiments investigating (A) the activity of Compounds 1-3 against MLL2 homozygous indel mutant cell lines SU-DHL-9 and Pfeiffer, and (B) the concentration dependence of Compound 3 inhibitory activity in SU-DHL-9 and Pfeiffer cell lines.

Compounds 1-3 (see Table 2) were tested in vitro for their ability to inhibit the growth of DoHH-2 (wild-type for MLL2), SU-DHL-9 and Pfeiffer (MLL2 homozygous indel mutants) cell lines. The results are shown in FIG. 2A. The concentration dependence of the activity of Compound 3 was also investigated. The results are shown in FIG. 2B.

Method:

Diffuse large B-cell lymphoma cell lines were maintained in RPMI medium 1640 (Life Technologies) supplemented with 10% (v/v) fetal bovine serum (Life Technologies) and 1% penicillin/streptomycin (Life Technologies) in a 37° C. incubator with 5% $CO_2$, humidified atmosphere. Cell line DOHH2 was obtained from DSMZ. Pfeiffer was obtained from ATCC. SU-DHL-9 was obtained from Martin Dyer (University of Leicester, UK).

Compounds were initially solubilized in DMSO at a concentration of 10 mM. This compound solution was further diluted 1:100 in RPMI medium 1640 to a final concentration of 100 μM. Ninety microliters of cells maintained at a concentration of $4 \times 10^5$ cells/mL were dispensed into wells of a MICROTEST™ 96-well Assay Plate, Optilux™ (BD). Ten microliters of the 100 μM compound solution were then added to the cells resulting in a final compound concentration of 10 μM. Each compound was tested in triplicate. Ten microliters of a 1:100 DMSO to RPMI medium 1640 solution were also added to 90 μL of cells as a carrier control. Furthermore, each plate included wells containing only RPMI medium 1640 to serve as a background noise control as well as cells that were completely untreated. Compounds were incubated with the cells in a 37° C. incubator with 5% $CO_2$, humidified atmosphere for 48 hours before being subjected to the alamarBlue® cell proliferation assay (Life Technologies). Raw fluorescent units were corrected for background noise and normalized to the carrier-treated control.

Example 4

In Vitro Activity of Compounds 2 and 3

The activity of Compound 3 in vitro was investigated further using the cell lines DoHH-2, OCI-LY3, WSU-DLCL2 (all wild-type for MLL2) and SU-DHL9. In addition, the dose response for Compound 2 was investigated in cell lines mutant for MLL2 or both MLL2 and EZH2. The dose response for Compound 3 was investigated in a MLL2 mutant cell line. Methods were as described for Example 3. Cell-line WSU-DLCL2 was obtained from DSMZ and OCI-Ly lines 3 was obtained from Louis Staudt (US National Institutes of Health).

Figure 3:
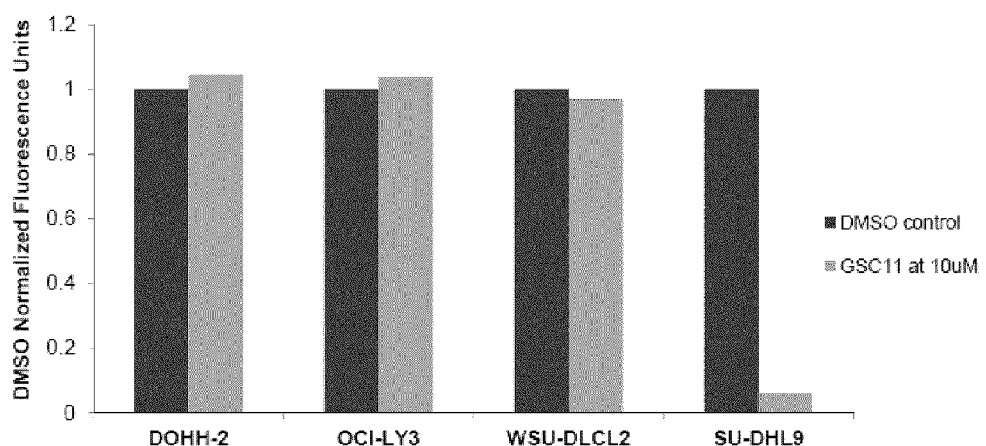
FIG. 3 presents the results of experiments demonstrating the specificity of cytotoxic effect of BPTF targeted compounds 2 and 3, (A) cytotoxicity of Compound 3 in different lymphoma cell lines, (B) dose response of Compound 3 in two MLL2 mutant cell lines and (C) dose response of Compound 2 in a MLL2 mutant cell line.
Figure 3:
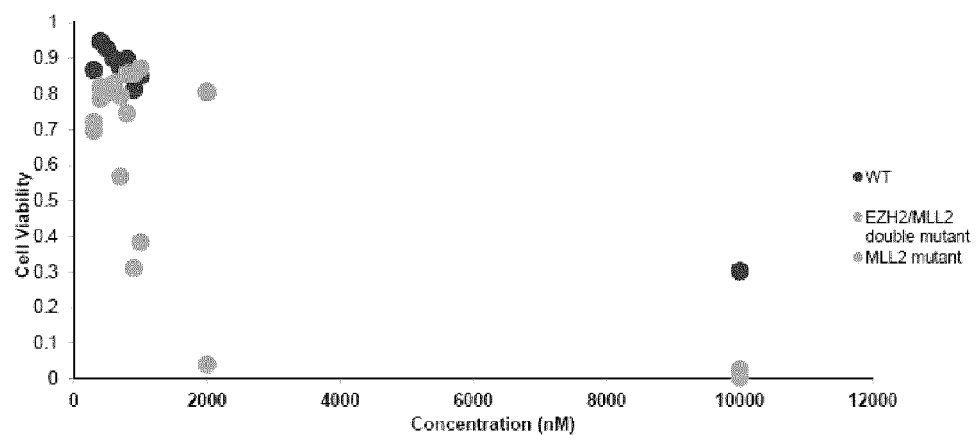

The results are shown in FIG. 3A-C. It should be noted that Compound 3 had no obvious effect on cells where MLL2 was wild-type, indicating that the compounds do not posses general toxic properties.

Example 5

Interaction of Compounds 2 and 3 with BPTF

In order to demonstrate that representative Compounds 2 and 3 interact with the BPTF target and influence its ability to bind the histone tail of H3, a BPTF pull down assay was employed. The assay is depicted schematically in FIG. 4 and described in detail below.

Figure 5:
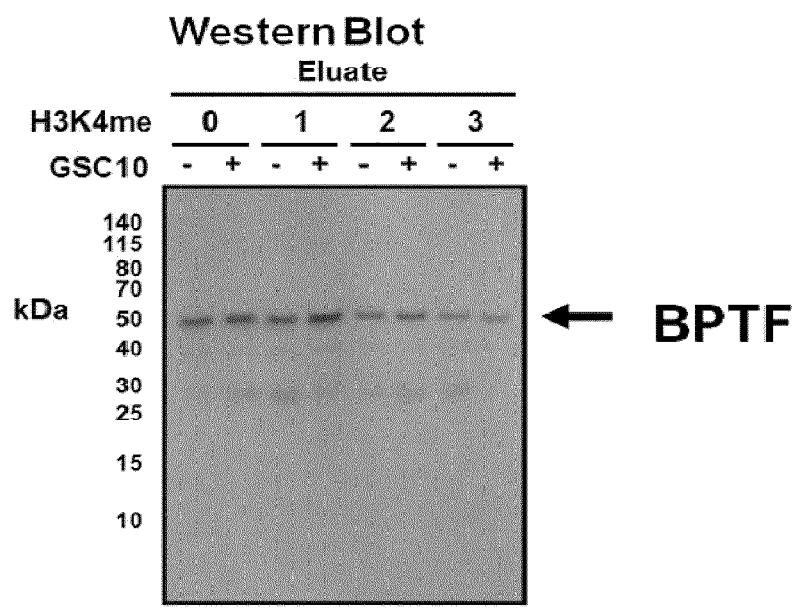
FIG. 5 presents Western blots showing the results of a pull down assay of H3K4 binding with BPTF in the presence and absence of (A) Compound 3, and (B) Compound 2.
Figure 5:
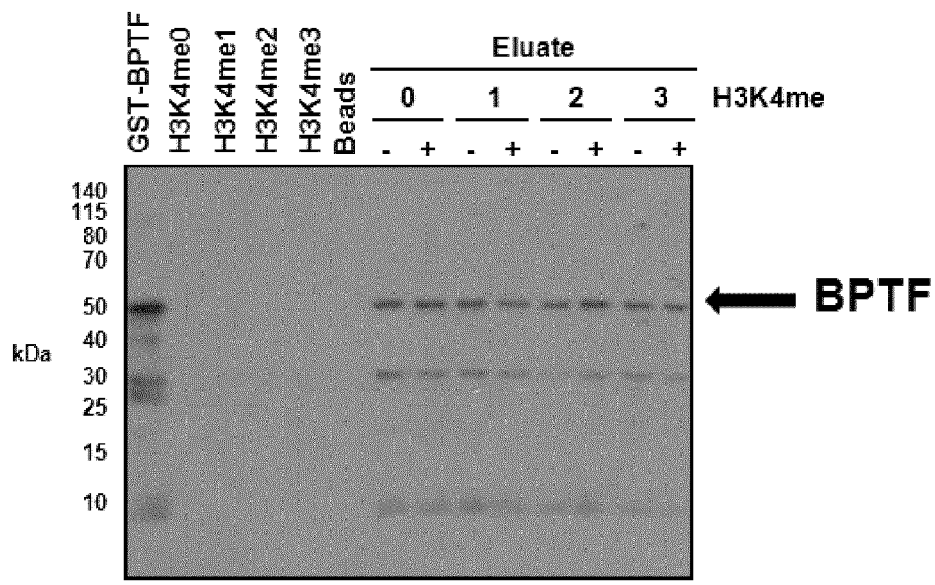

Using this assay, it was determined that Compound 3 was able to stabilize the binding of H3K4me1 with BPTF (FIG. 5A), whereas serendipitously Compound 2 was able to stabilize the binding of H3K4me2 (FIG. 5B). In FIG. 5A, the GST antibody staining shows increased BPTF protein in the presence of Compound 3 and H3K4me1 and diminished binding in the presence of the compound and H3K4me3. Densitometry values H3K4me1+Compound 3=13335, H3K4me–Compound 3=9350, H3K4me3+Compound 3=4227, H3K4me3–Compound 3=2545. In FIG. 5B, the GST antibody staining shows increased BPTF protein in the presence of Compound 2 and H3K4me2 and diminished binding in the presence of the compound and H3K4me3.

Method:

The full-length human BPTF construct was obtained from C. David Allis of the Laboratory of Chromatin Biology, Rockefeller University (Li et al., 2006, ibid). The dual PHD finger-bromodomain (residues 2583-2751) from the human BPTF (gi:31322942) was cloned into a pDEST15 vector using Gateway® cloning technology allowing for an N-terminal GST tag (Life Technologies). Over-expression of the GST-BPTF dual PHD finger-bromodomain was induced in BL21-AI™ chemically competent *E. coli* cells using LB medium supplemented with 1 mM IPTG and 0.2% L-arabinose for 2 hours in a 37° C. shaking incubator. GST-BPTF dual PHD finger-bromodomain was purified using Glutathione Sepharose 4B media (GE Healthcare Life Sciences) and dialyzed against PBS (Life Technologies) overnight.

The peptide pull-down experiment was performed essentially as previously described (Ruthenburg et al., 2011, *Cell*, 145(5):692-706.). Fifty microliters of M-280 streptavidin-coupled Dynabeads® (Life Technologies) were dispensed into 1.5 mL microtubes and washed 3×50 µL in PBS. The beads were then incubated with C-terminally biotinylated H3K4me0, me1, me2 or me3 peptides 21 amino acids long (Anaspec) rotating for 1 hour at 4° C. under saturating conditions. The beads were washed 3×100 µL in HBS-TD (10 mM Na-HEPES, 150 mM NaCl, 0.005% Tween-20, 2 mM DTT) and incubated with 6.8 µM of GST-BPTF along with either 68 µM of drug in a 1:100 DMSO to PBS solution or carrier alone rotating for 3 hours at 4° C. The beads were then washed 10×200 µL in HBS-TD. The protein was eluted using 2×LDS sample buffer (Life Technologies) and 1× reducing agent (Life Technologies) at 85° C. for 10 minutes. Samples were subjected to SDS-PAGE and bands were visualized using either SimplyBlue stain (Life Technologies) or GST antibody (Santa Cruz). Quantification of bands was made using ImageJ software.

Example 6

In Vivo Activity of Compound 3

Compounds 2 and 3 were tested for their ability to decrease the growth of tumours in a mouse xenograft model.

Xenograft Models.

NOD/SCID/$\gamma^{null}$ (NSG) mice were bred at the local BCCRC animal facility. To establish primary tumors, male NSG mice were inoculated with $1\times10^7$ cells of the human diffuse histiocytic lymphoma cell line SU-DHL-9 in 50 µl PBS in the flank area. After development of s.c. tumors, mice were sacrificed and small fragments of the tumors (~20 mg) were transplanted s.c. into the right flank of anesthetized six-ten weeks old male NSG recipient mice using 13 G trocar needles. Treatment was initiated once the tumors became palpable. Tumourlength and width was determined by caliper and tumourvolume was calculated by the modified ellipsoidal formula as (length×width)/2.

Efficacy Studies.

Compounds were diluted in a mixture of 50% DMSO and 50% polyethylene glycol 200. Eight tumor-bearing mice per group were administered by intraperitoneal injections daily over a period of eight days with either compounds at doses of 1 mg/kg or 4 mg/kg (Compound 3; NSC 127763), 4 mg or 12 mg/kg (Compound 2; NSC 304107) or the vehicle for control. Body weight was recorded every two days, tumoursize every four days and mice were monitored for any other additional adverse effects. Experimental animals were sacrificed at day nine, tumourvolumes were determined and the significance of differences was determined by Student's t-test after normalizing to the initial tumourvolume.

Figure 6:
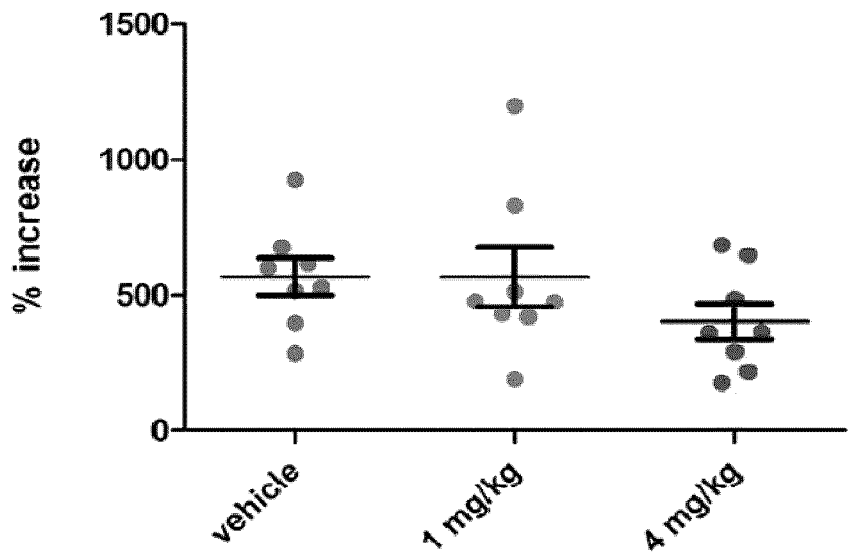
FIG. 6 presents the results of in vivo testing of Compounds 2 and 3 in a mouse xenograft model, (A) Compound 3 and (B) Compound 2, showed a reduction in tumour increase over a 9-day period using the SU-DHL-9 (MLL2 mutated) cell-line in a mouse xenograft model.
Figure 6:
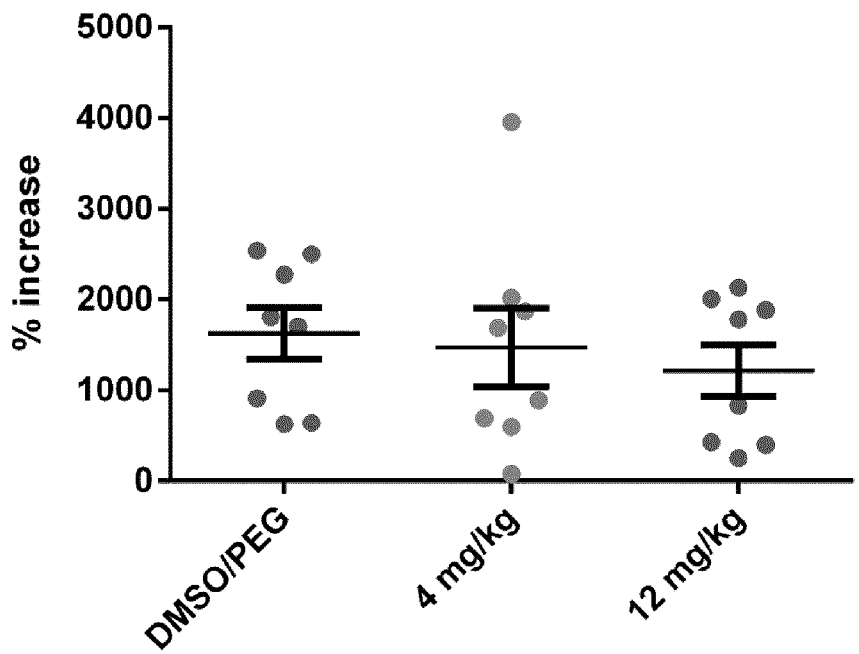

As shown in FIG. 6, both compounds showed anti-tumour activity in this mouse xenograft model. For Compound 3 (FIG. 6A), in this fast growing model the presence of the compound at the relatively low-level of 4 mg/kg, was able to reduce the median tumour growth to 362% compared to the untreated control which had a median tumour growth of 563%. Compound 2 (FIG. 6B) at a dosage of 12 mg/kg was able to reduce the median tumour growth to 1305% compared to the untreated control which had a median tumour growth of 1755%. These results are especially promising as the dosing or formulation of these compounds was not optimized.

Example 7

Small Molecule Reprogramming of CBX2

A computational approach was applied to the histone methylation mark reader CBX2 based on the structure of the fly Policomb protein (an analogue of CBX2) resulting in the identification of a number of candidate CBX2 reprogramming compounds (Table 5).

Pharmacophore Description:

CBX2 binds positively charged methylated epigenetic marks with an aromatic cage formed by three residues: F11, W22 and W25. Unlike BPTF whose aromatic cage is formed by 4 residues, CBX2 has an open face structure. A sufficiently large aromatic group of a compound can thus be used to complete formation of the more usual, 4-face aromatic cage typical for methylated Lys binders. Similar to BPTF, stabilization of a triple reprogramming complex of CBX2, a H3K27H[3,2,1]me[0,1,2] peptide and a reprogramming compound can be achieved with a hydrogen bond between the partially methylated Lys27 and the compound. Absence of such hydrogen bonding in the aromatic cage is likely responsible for the selective affinity of CBX2 for the K27me3 mark. For the reprogramming compounds shown in Table 5, the presence of hydrogen acceptor in proximity of a larger aromatic moiety is a critical component that is predicted to be responsible for perturbing the natural affinity of CBX2 for the trimethylated histone tail. The additional hydrogen acceptor motif provided by the compounds explains superiority of those compounds that include a ketone motif near a naphthalene-like moiety over a hydroxyl motif. A similar argument would apply to the apparent superiority of compounds containing a $R_2NH$ moiety over those including a $R_4N$ moiety. A hydrophobic moiety as the second flanking component of hydrogen acceptor motif may also be important and can be explained by the long hydrocarbon part of the Lys27me2 sidechain. While the aromatic cage in the active site interacts with the lysine methylated nitrogen, the hydrocarbons Cβ, Cγ and Cδ are open to polar water media. Accordingly, it is predicted that a reasonably large moiety, such as $CH_2Br$ or $CH_2Ph$ (in case of NSC14755), covers this zone of the H3 peptide and additionally contributes to the stability of the complex.

TABLE 5

Candidate CBX2 Re-Programming Compounds

| | | | Effect on Cell Viability (% survival) | |
|---|---|---|---|---|
| Compound | Structure | NSC No. | DoHH2 Cells | WSU-DLCL2 Cells |
| 25 | [structure] | NSC40830 | 100 | 60 |
| 26 | [structure] | NSC400906 | 100 | 90 |
| 27 | [structure] | NSC25671 | 90 | 40 |
| 28 | [structure] | NSC25767 | 100 | 100 |
| 29 | [structure] | NSC25676 | 100 | 80 |

TABLE 5-continued

Candidate CBX2 Re-Programming Compounds

| Compound | Structure | NSC No. | Effect on Cell Viability (% survival) | |
|---|---|---|---|---|
| | | | DoHH2 Cells | WSU-DLCL2 Cells |
| 30 | (structure) | NSC40304 | 60 | 40 |
| 31 | (structure) | NSC40409 | 100 | 100 |
| 32 | (structure) | NSC112362 | 100 | 90 |
| 33 | (structure) | NSC402675 | 100 | 100 |
| 34 | (structure) | NSC402677 | 100 | 90 |

TABLE 5-continued

Candidate CBX2 Re-Programming Compounds

| Compound | Structure | NSC No. | Effect on Cell Viability (% survival) | |
|---|---|---|---|---|
| | | | DoHH2 Cells | WSU-DLCL2 Cells |
| 35 | (quinoline with 2-(4-chlorophenyl), 8-phenyl, 4-C(O)CH2Br) | NSC40004 | 20 | 17 |
| 36 | (quinoline with 2-(4-chlorophenyl), 8-phenyl, 4-CH(OH)CH2Br) | NSC400930 | 100 | 90 |
| 37 | (quinoline with 2-(4-chlorophenyl), 8-phenyl, 4-C(O)Cl) | NSC400924 | 100 | 80 |
| 38 | (quinoline with 2-(4-chlorophenyl), 7-chloro, 4-CH(OH)(piperidin-1-yl)) | NSC5489 | 100 | 80 |

TABLE 5-continued

Candidate CBX2 Re-Programming Compounds

| Compound | Structure | NSC No. | Effect on Cell Viability (% survival) | |
|---|---|---|---|---|
| | | | DoHH2 Cells | WSU-DLCL2 Cells |
| 39 | | NSC23924 | 60 | 20 |
| 40 | | NSC13316 | 100 | 50 |
| 41 | | NSC14224 | 17 | 10 |
| 42 | | NSC305758 | 30 | 10 |
| 43 | | NSC16001 | 40 | 10 |

TABLE 5-continued

Candidate CBX2 Re-Programming Compounds

| Compound | Structure | NSC No. | Effect on Cell Viability (% survival) | |
|---|---|---|---|---|
| | | | DoHH2 Cells | WSU-DLCL2 Cells |
| 44 | | NSC13480 | 10 | 10 |
| 45 | | NSC4378 | 100 | 80 |
| 46 | | NSC401591 | 100 | 90 |
| 47 | | NSC32936 | 100 | 100 |
| 48 | | NSC146840 | 90 | 40 |

TABLE 5-continued

Candidate CBX2 Re-Programming Compounds

| Compound | Structure | NSC No. | Effect on Cell Viability (% survival) | |
|---|---|---|---|---|
| | | | DoHH2 Cells | WSU-DLCL2 Cells |
| 49 | *[structure: 7-chloro-8-methyl-2-(4-chlorophenyl)quinoline with C(=O)CH2NH-benzyl at 4-position]* | NSC14755 | 70 | 50 |
| 50 | *[structure: 2-phenyl-6,8-dichloroquinoline with C(=O)CH2Br at 4-position]* | NSC112372 | | |
| 51 | *[structure: 2-(3,4-dichlorophenyl)quinoline with CH(OH)-piperidin-2-yl at 4-position]* | NSC2450 | | |

Example 8

In Vitro Activity of Compound 50

Lymphoid malignancies with various mutations in the EZH2 gene have been shown to have increased activity of PRC2 in tri-methylating the histone H3 at the residue Lysine 27 (H3K27). Compound 50 was tested for its effect on the viability of three lymphoma cell lines in vitro using standard methods. The cell lines tested were: DoHH-2 (wildtype for EZH2, MEF2B and MLL2); WSU-DLCL2 (EZH2 mutation Y641F (wildtype for MEF2B and MLL2)) and DB (EZH2 mutation Y641N, the MEF2B mutation D83V and three mutations in MLL2 (two of which lead to a truncated protein after residue Q2736 and the third allele has a 1 base pair deletion at residue P480)).

Figure 7:
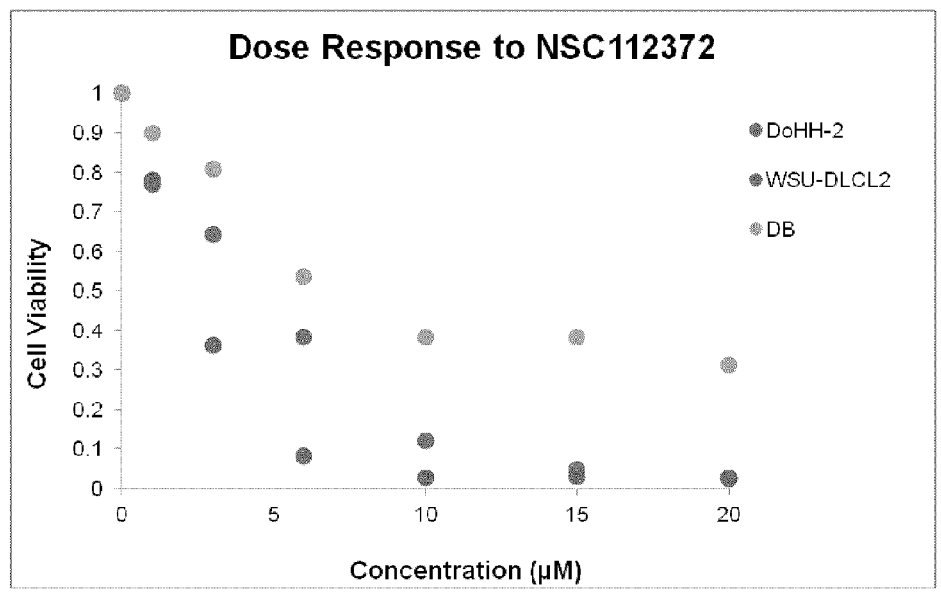
FIG. 7 presents the results of an in vitro assay to determine cell viability of various lymphoma cell lines in the presence of Compound 50 (NSC112372); DoHH-2: wildtype for EZH2, MEF2B and MLL2; WSU-DLCL2: EZH2 mutation Y641F (wildtype for MEF2B and MLL2); DB: EZH2 mutation Y641N, the MEF2B mutation D83V and three mutations in MLL2.

The results are shown in FIG. 7 and indicate that Compound 50 reduced the viability of all three cell lines in a dose dependent manner, but showed the highest activity against the cell-line WSU-DLCL2 which possesses the EZH2 Y641 mutation.

Example 8

Effect of Compound 50 on Tumour Growth in a Mouse Xenograft Model

WSU-DLCL2 tumourfragments were transplanted subcutaneously into the flank of male NSG mice. Mice were 9.0-9.3 weeks at transplantation and treatment was started when the mice were between 12.9 and 13.1 weeks. 8 mice were used per group and treatment was daily for ten days with evaluation at day 12. Tumoursize determined by caliper every four days, tumourvolume calculated by length× width$^2$/2.

The groups of mice were treated with vehicle (control), 1 mg/kg Compound 50 or 4 mg/kg Compound 50 by intraperitoneal injection. Vehicle was 50% DMSO/50% PEG-400.

Figure 8:
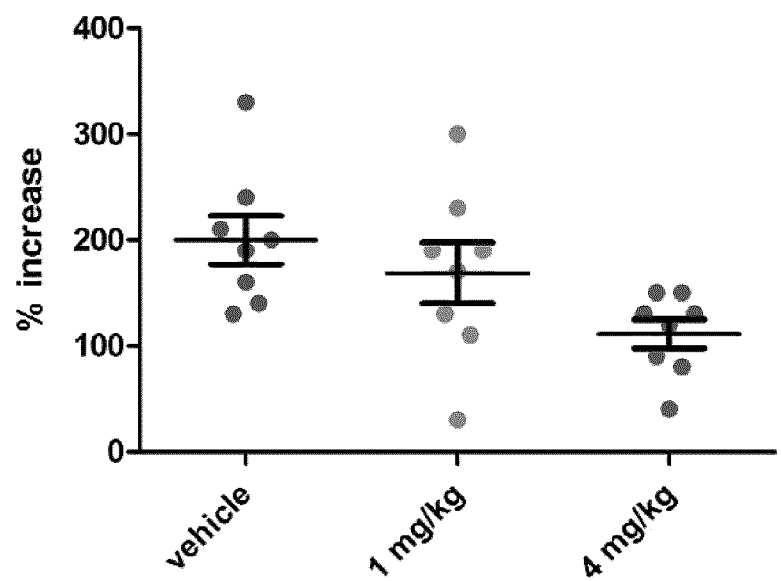
FIG. 8 presents the results from xenograft experiments using the WSU-DLCL2 human diffuse large cell lymphoma cell line in which mice were treated with vehicle, 1 mg/kg or 4 mg/kg Compound 50 (p=0.0047 between control and 4 mg/kg groups).

The results are shown in FIG. 8 and demonstrate that Compound 50 at both dosages was able to reduce tumour volume.

Example 10

Effect of Compound 51 on Proliferation of Lymphoma Cell Lines

Compound 51 (NSC2540) was tested for its effect on the viability of four lymphoma cell lines in vitro using standard methods. The cell lines tested were DoHH-2, WSU-DLCL2, DB and SU-DHL-9 (EZH2 wildtype, MEF2B wildtype, MLL2 indel).

Figure 9:
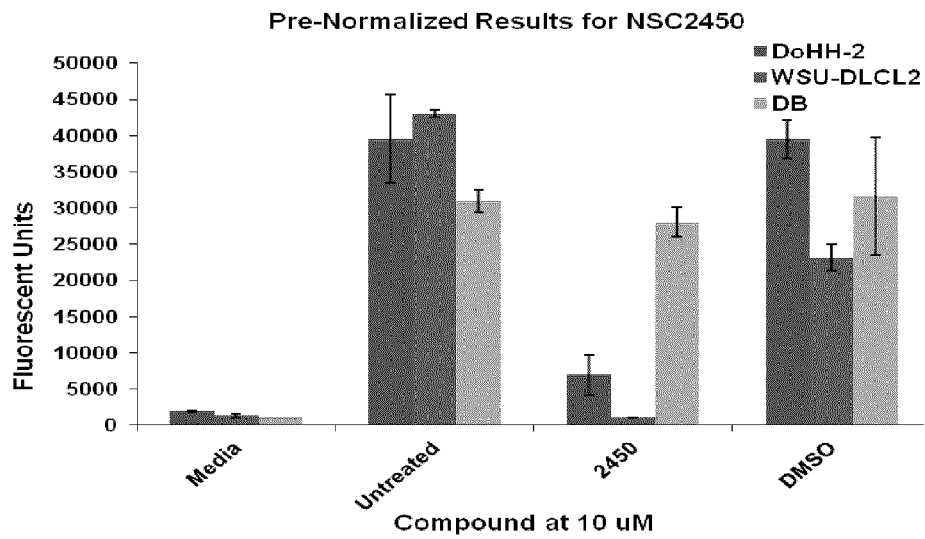
FIG. 9 presents the results of in vitro assays to determine cell viability of various lymphoma cell lines in the presence of Compound 51 (NSC2450) (cell lines as in FIG. 1; SU-DHL-9: EZH2 wildtype, MEF2B wildtype, MLL2 indel).
Figure 9:
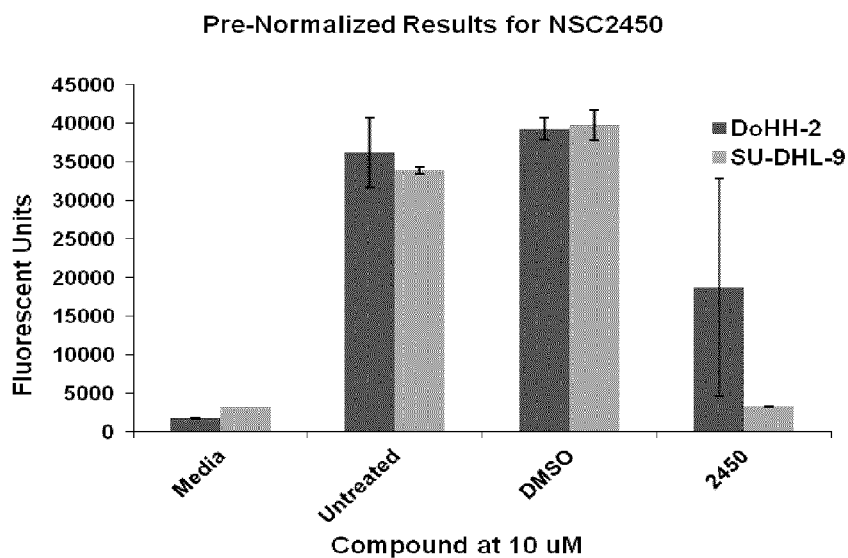

The results are shown in FIG. 9 and demonstrate that Compound 51 was able to decrease viability of the DoHH-2, WSU-DLCL2 and SU-DHL-9 cell lines.

Example 11

Effect of Compound 51 on Tumour Growth in a Mouse Xenograft Model

WSU-DLCL2 tumourfragments were transplanted subcutaneously into the flank of male NSG mice. Mice were 5.3-9.4 weeks at transplantation and treatment was started when the mice were between 8.6 and 12.7 weeks. 8 mice were used in the control group and 6 mice were used in the Compound 51 treated group. Treatment was daily for ten days with evaluation at day 12. Tumoursize determined by caliper every four days, tumourvolume calculated by length×width$^2$/2.

The groups of mice were treated with vehicle (control) or Compound 51 by intraperitoneal injection at 4 mg/kg for the first 5 days and 2 mg/kg for the subsequent 5 days. Vehicle was 50% DMSO/50% PEG-400.

Figure 10:
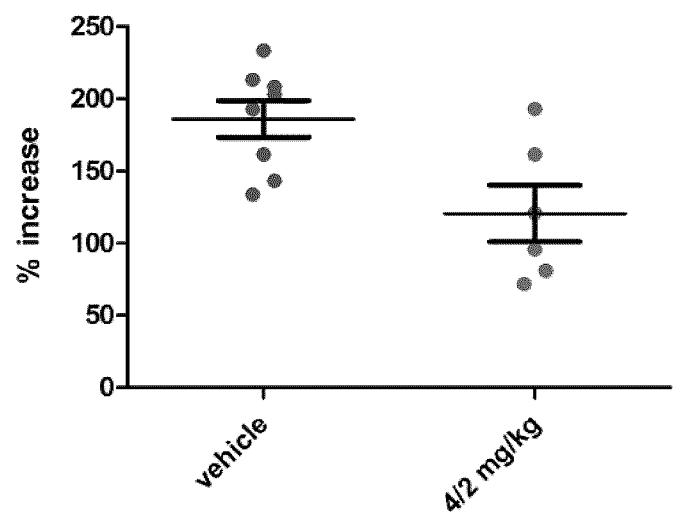
FIG. 10 presents the results from xenograft experiments using the WSU-DLCL2 human diffuse large cell lymphoma cell line in which mice were treated with vehicle or Compound 51 at 4 mg/kg for 5 days followed by 2 mg/kg for five days (p=0.0125).

The results are shown in FIG. 10 and demonstrate that Compound 51 was able to significantly reduce tumourvolume.

Example 12

Effect of Compounds 50 and 51 on Proliferation of Breast Cancer Cell Lines

Compounds 50 and 51 were tested for their effect on the viability of four breast cancer cell lines in vitro using standard methods. The cell lines tested were: MCF-7, MDA-MB-231, HCC202 (CRL-2316) and HCC1500 (CRL-2329).

Figure 11:
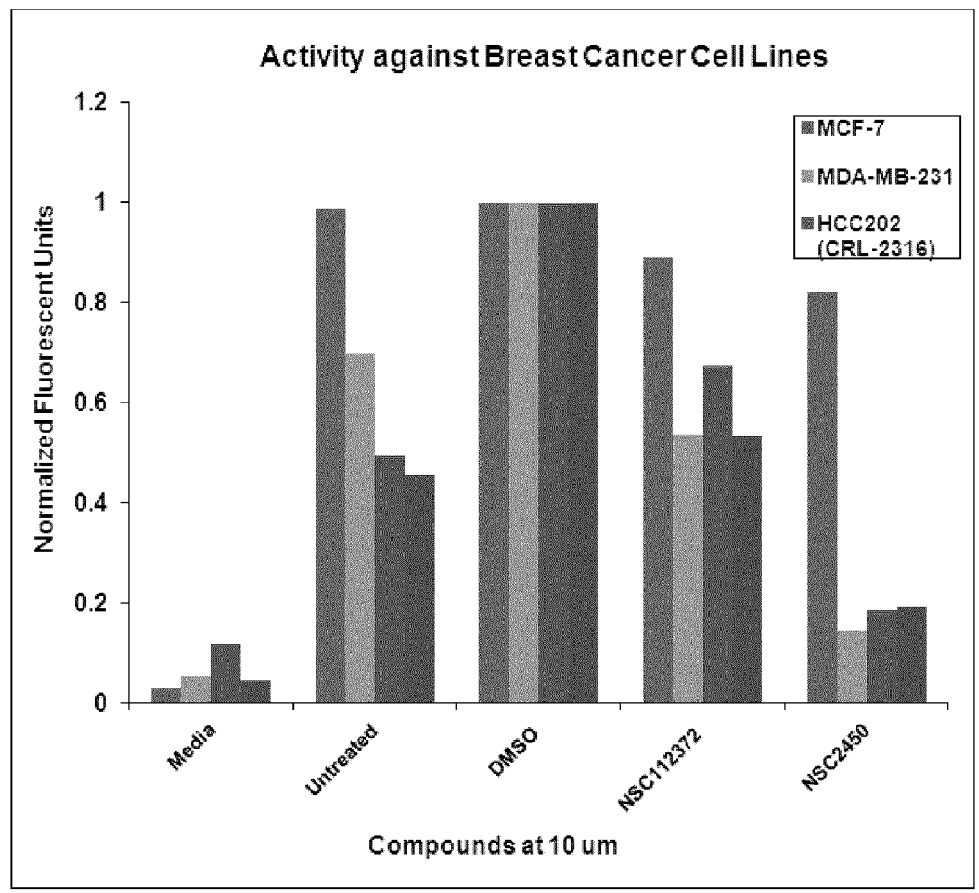
FIG. 11 presents the results of in vitro assays to determine cell viability of various breast cancer cell lines in the presence of Compound 50 or Compound 51.
Figure 12:
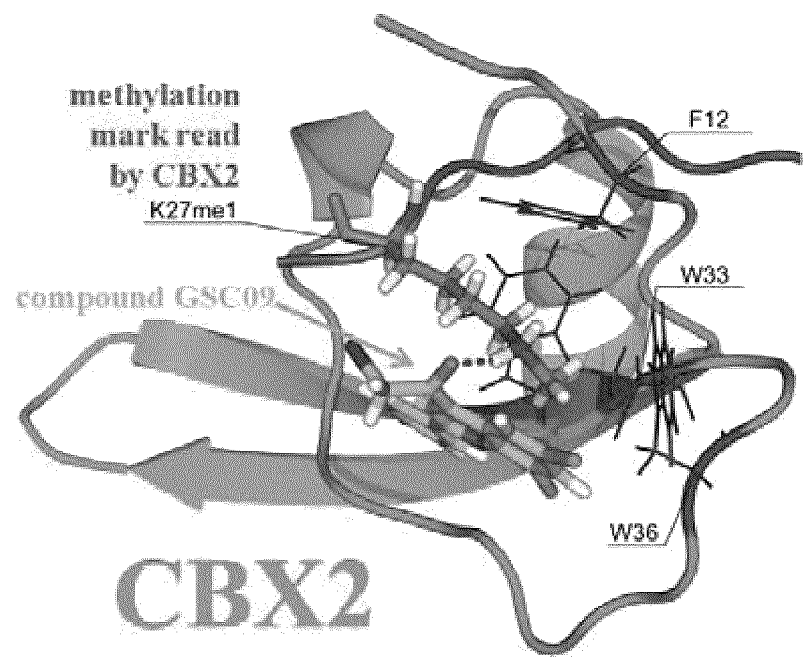
FIG. 12 presents a model of a "triple reprogramming complex" of CBX2, a CBX2 reprogramming compound and the H3K4me1 peptide.

The results are shown in FIG. 11 and demonstrate that Compound 51 was able to decrease viability of the MDA-MB-231, HCC202 (CRL-2316) and HCC1500 (CRL-2329) cell lines.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

What is claimed is:

1. A method for identifying a candidate compound that increases binding of a histone mark reader protein to a target histone tail mark, the method comprising:

(a) computationally generating a structural model of the active site of the reader protein in complex with the target histone tail mark, the structural model based on a computational model of the active site of the reader protein complexed with its cognate histone tail mark;

(b) identifying one or more functional features required for binding of the target histone tail mark in the active site of the reader protein;

(c) modeling into the active site a virtual probe structure that, together with residues in the active site and the target histone tail mark, substantially reproduces the functional features identified in step (b) to form a stable complex comprising the target histone tail mark, the residues of the active site and the virtual probe structure;

(d) modeling candidate compounds in place of the virtual probe structure to identify a candidate compound which forms a stable complex comprising the target histone tail mark, the residues of the active site and the identified candidate compound;

(e) providing the candidate compound identified in step (d) for use in one or more in vitro assays to assess increased binding of the histone mark reader protein to the histone tail mark; and (f) testing the candidate compound provided in step (e) in the one or more in vitro assays to assess increased binding of the reader protein to the target histone tail mark.

2. The method according to claim 1, wherein step (c) comprises conducting an iterative molecular dynamics simulation of a series of virtual probe structures in the active site with the target histone tail mark to identify an optimal probe structure that provides the stable complex comprising the target histone tail mark, the residues of the active site and the virtual probe structure.

3. The method according to claim 2, wherein step (d) comprises docking the candidate compounds into an average protein structure based on the stable complex comprising the target histone tail mark, the residues of the active site and the virtual probe structure.

4. The method according to claim 1, wherein step (d) comprises performing molecular dynamics simulations, in silico docking methods, structural similarity searching, or a combination thereof.

5. The method according to claim 1, wherein the target histone tail mark and the cognate histone tail mark are methylated lysine marks.

6. The method according to claim 5, wherein the cognate histone tail mark is a trimethylated lysine and the target histone tail mark is a di-, mono- or un-methylated lysine.

7. The method according to claim 6, wherein the one or more functional features include an aromatic cage formed by 3 or more aromatic residues in the active site.

8. The method according to claim 6, wherein the one or more functional features comprise a hydrogen bond.

9. The method according to claim 1, wherein the cognate histone tail mark is a trimethylated lysine and the target histone tail mark is a di-, mono- or un-methylated lysine, and wherein the virtual probe structure comprises a hydrogen acceptor.

10. The method according to claim 9, wherein the virtual probe structure further comprises a 6-membered aliphatic or aromatic ring structure.

11. The method according to claim 1, wherein the candidate compounds are selected from a virtual small molecule library.

12. The method according to claim 1, wherein the histone mark reader protein is CBX2 or BPTF.

13. The method according to claim 12, wherein the candidate compound identified in step (d) is a candidate for treatment of a cancer characterized by increased methylation activity of EZH2, or a cancer characterized by decreased methylation activity of MLL2.

* * * * *